(12) United States Patent
Pandha et al.

(10) Patent No.: US 8,460,882 B2
(45) Date of Patent: Jun. 11, 2013

(54) CANCER BIOMARKERS

(75) Inventors: Hardev Pandha, London (GB);
Richard George Leonard Morgan, Surrey (GB)

(73) Assignee: The University of Surrey, Surrey (GB)

(*) Notice: Subject to any disclaimer, the term of this patent is extended or adjusted under 35 U.S.C. 154(b) by 837 days.

(21) Appl. No.: 12/518,708

(22) PCT Filed: Dec. 19, 2007

(86) PCT No.: PCT/GB2007/004902
§ 371 (c)(1),
(2), (4) Date: Oct. 29, 2009

(87) PCT Pub. No.: WO2008/075056
PCT Pub. Date: Jun. 26, 2008

(65) Prior Publication Data
US 2010/0093558 A1    Apr. 15, 2010

(30) Foreign Application Priority Data

Dec. 19, 2006 (GB) .................................. 0625321.5
Oct. 10, 2007 (GB) .................................. 0719792.4

(51) Int. Cl.
G01N 33/53     (2006.01)
G01N 33/567    (2006.01)
G01N 33/574    (2006.01)
C07K 14/00     (2006.01)
A61K 38/16     (2006.01)

(52) U.S. Cl.
USPC .......... 435/7.1; 435/7.21; 435/7.23; 530/350; 530/358

(58) Field of Classification Search
None
See application file for complete search history.

(56) References Cited

U.S. PATENT DOCUMENTS

2005/0042650 A1* 2/2005 Sauvageau et al. .............. 435/6
2005/0079492 A1* 4/2005 Burgess, Jr. et al. ............. 435/6

FOREIGN PATENT DOCUMENTS

| WO | WO-99/00498 A1 | 1/1999 |
| WO | WO 03/053223 A2 * | 7/2003 |
| WO | WO 2006/071466 A2 * | 7/2006 |
| WO | WO-2006071466 A2 | 7/2006 |
| WO | WO-2006089091 A2 | 8/2006 |

OTHER PUBLICATIONS

Molecular Probes® Products (Qdot® Nanocrystals, http://www.invitrogen.com/site/us/en/home/brands/Molecular-Probes/Key-Molecular-Probes-Products/Qdot.html?s_kwcid=TC|12303|qdots||S|b|8516649974&cid=covinvgg|89100000002316s, Feb. 17, 2012).*
Morgan and Pandha (Amer. Assoc. Cancer Research, 97th Annual Meeting, Apr. 3, 2006, Abstract #2641).*
Neely et al. (The Laryngoscope, Oct. 2003 113:1719-1725).*
Burden, H. et al., "A Novel Test for Prostate Disease," *Eur Urol Suppl* (2006);5:798.
Bose, S. et al., "EN2 is a potential candidate oncogene in prostate cancer," *Proceedings of the American Associate for Cancer Research* (2007);48:503.
Lavezzi, A., et al, "Involvement of the *EN-2* gene in normal and abnormal development of the human arcuate nucleus," *Int. J. Exp. Path.* (2005); 86:25-31.
Miller, G.J., et al., "Aberrant *HOXC* Expression Accompanies the Malignant Phenotype in Human Prostate," Cancer Research (Sep. 15, 2001);63:5879-5888.
Morgan, R., et al., "Prostate cancer cells express and secrete the *Engrailed* transcription factor," Proc. Amer. Assoc. Cancer Res., 97th Annual Meeting, Apr. 3, 2006, Abstract #2641.

* cited by examiner

*Primary Examiner* — Peter J Reddig
(74) *Attorney, Agent, or Firm* — McCarter & English, LLP; Maria Laccotripe Zacharakis

(57) ABSTRACT

Provided is a biomarker for detecting cancer, in particular prostate cancer in a male subject, the biomarker comprising at least one homeodomain containing transcription factor, such as a HOX peptide or EN-2 peptide, or a fragment thereof. The use of said biomarker in detecting and/or treating prostate cancer is provided, together with methods and kits therefor.

18 Claims, 7 Drawing Sheets

CANCER BIOMARKERS

SEQUENCE LISTING

The instant application contains a Sequence Listing which has been submitted via EFS-Web and is hereby incorporated by reference in its entirety. The ASCII copy of the Sequence Listing, created on Jul. 8, 2009, is named seq1st.txt, and is 24,233 bytes in size.

The present invention relates to the use of at least one homeodomain containing transcription factor, such as a HOX peptide or EN-2 peptide, as a biomarker for prostate cancer.

Prostate cancer is currently the leading cause of cancer related death in men, killing 10,000 men each year in the UK alone. However, the current availability of biomarkers for the non-invasive detection of prostate cancer is essentially limited to Prostate Specific Antigen (PSA). Serum levels of PSA are significantly raised in prostate cancer patients, and the PSA test is currently used to follow the progress of the disease and its response to treatment.

Unfortunately, there are a number of significant disadvantages with the PSA test. As PSA levels are also significantly raised in other, non-cancerous conditions of the prostate, such as prostatitis and benign hypertrophy, it is not always certain that detecting an increase in PSA levels is actually indicative of prostate cancer in a patient. Furthermore, PSA levels do not necessarily correlate with the volume of the disease or to the development of nodal or bone metastasis.

Recent attempts to use indicia such as the ratio of free to total PSA and "PSA velocity" proved largely unsuccessful, due to the very high level of false positives, resulting in a large number of unnecessary invasive biopsies.

Indeed, the levels of PSA are thought to rise only very slowly in prostate cancer, so that the disease is often far advanced before a positive result is obtained, when measuring PSA levels. Furthermore, PSA levels have to be normalised, as they can vary with age and prostate size.

There are also a number of additional potential chemical markers of prostate cancer including the kallikreins, and more recently, the 80 kDa fragments of e-cadherin (Kuefer et al., 2005). Again, these biomarkers tend to show many of the significant disadvantages discussed above in relation to PSA.

Thus, there is a need in the art for a reliable prostate cancer biomarker.

Surprisingly, we have found that a homeotic transcription factor, HOXC4, is secreted from prostate tumours and its serum concentration is significantly elevated in patients of prostate cancer. Thus, the presence of HOXC4 in body fluids, such as the serum, is a useful indicator of both early and late stage prostate cancer.

We have also found that a second HOX protein, HOXB6, and a third protein HOXB5, also show similar results. HOXA3 and HOXD9 are also considered to be useful as biomarkers.

We have further identified the homeodomain-containing transcription factor Engrailed 2 (EN-2) as being expressed at both the RNA and protein level in the prostate cancer-derived cell lines LNCaP and PC3, and also in primary prostate cancer cells. Furthermore, the EN-2 protein can be secreted into the surrounding medium of the cells.

Surprisingly, elevated levels of all these cancer markers could be detected in prostate cancer patients even when the PSA levels were found to be normal. This further illustrates that the markers of the present invention are more reliable in the diagnosis of prostate cancer when compared to other markers, such as PSA.

Thus, in a first aspect, the present invention provides the use of at least one homeodomain-containing transcription factor, or a fragment thereof, as a biomarker for prostate cancer. Examples of homeodomain-containing transcription factors include HOX and EN-2 peptides. The invention also relates to a method for diagnosing prostate cancer disease comprising detecting at least one homeodomain-containing transcription factor in a sample from a patient.

It is particularly preferred that the at least one HOX or EN-2 peptide, or a fragment thereof, is detectable in a body fluid.

Preferably the biomarker is HOXC4 alone. It is also preferred that the biomarker is HOXB5 alone or more preferably HOXB6 alone. It is also preferred that the biomarker is EN-2 alone. It is also preferred that the biomarker is HOXA3 alone. It is also preferred that the biomarker is HOXD9 alone. However, combinations are also preferred. Such combinations include HOXC4 and HOXB5; HOXC4 and HOXB6; HOXB5 and HOXB6; HOXC4, HOXB5 and HOXB6; EN-2 and HOXC4; EN-2 and HOXB5; EN-2 and HOXB6; EN-2, HOXC4 and HOXB5; EN-2, HOXC4 and HOXB6; EN-2, HOXB5 and HOXB6; EN-2, HOXC4, HOXB5 and HOXB6. Such combinations may also further comprise one or both of HOXA3 and/or HOXD9. Further combinations include HOXA3 and HOXD9; HOXA3 and HOXC4; HOXA3 and HOXB5; HOXA3 and HOXB6; HOXA3 and EN-2; HOXD9 and HOXC4; HOXD9 and HOXB5; HOXD9 and HOXB6; HOXD9 and EN-2. A particularly preferred combination of markers comprises one or more of, preferably all of, HOXC4, HOXB5, HOXB6 and EN-2.

Preferably, the body fluid is the serum or urine. Other preferred body fluids are discussed below.

The HOX genes are a family of homeodomain-containing transcription factors that determine the identity of cells and tissues during early development (reviewed by Morgan, 2006). Recent publications, including Miller et al 2003, have effectively identified every single protein that is expressed, and retained intracellularly, in a prostate cancer tumour cell. Of course, this means that a total of around 10,000 to 12,000 proteins, including the HOX peptides, were identified.

However, we have surprisingly discovered that, from amongst these thousands of proteins expressed in prostate cancer cells, the HOXC4 protein, for instance, is found extracellularly and is an excellent biomarker for prostate cancer.

This is surprising for a number of reasons. Firstly, HOXC4 is a transcription factor and, therefore, you would not expect to find it in the serum. Secondly, although other biomarkers for prostate cancer are known, finding a reliable biomarker has remained elusive, see for instance the problems described above in relation to PSA. Indeed, HOXC4 is both an early stage and, in particular, a late stage biomarker, as shown in FIG. 1.

Thus, this protein has not been identified as a biomarker for prostate cancer before although it is known to be expressed in prostate cancer cells, along with many thousands of other proteins, many of which could not be described as biomarkers for prostate cancer. This also applies to other HOX peptides including HOXB5 and HOXB6.

Like the HOX peptides, the Engrailed (En) proteins are also homeodomain-containing transcription factors that show a very high degree of functional conservation during development (reviewed by Morgan, 2006). The original En gene was characterised in Drosophila, where the En mutant fails to form a border between the anterior and posterior wing (Garcia-Bellido and Santamaria, 1972). Vertebrate homologues of En likewise have regulatory roles during development, which include limb development and both the early specification and subsequent axonal migrations of the nervous system (Morgan 2006).

In addition to transcriptional regulation, EN proteins have a number of other, apparently unrelated properties that are functionally important. The first of these is the ability to be secreted from cells, and to be internalized by others (Cosgaya et al., 1998; Joliot et al., 1998, reviewed by Morgan, 2006). The exact mechanistic basis for this phenomenon is unknown, although it is clear that it depends upon a conserved nuclear export sequence located in the homeodomain (Maizel et al., 1999; Chatelin et al., 1996; Derossi et al., 1996; Joliot et al., 1997).

In addition to its developmental role, EN-2 has recently been shown to be a potential oncogene in breast cancer (Martin et al., 2005). Non-tumorogenic murine mammary cell lines forced to express EN-2 subsequently exhibit a number of malignant characteristics including a shortening of the cell cycle and a loss of cell to cell contact. Further, RNAi silencing of EN-2 indicates that it is required for the maintenance of the transformed phenotype in a human breast cancer cell line.

We have discovered that EN-2 is overexpressed and secreted from the prostate cancer derived cell line LNCaP and in human tissue samples from prostatic adenocarcinoma. Furthermore, EN-2 is secreted from ductal cells and adenocarcinoma tumours and is present in the urine of prostate cancer patients. This is the first time that EN-2 has been suggested as a marker of prostate cancer.

Preferably, presence or absence of the at least one homeodomain-containing transcription factor, such as a HOX peptide or EN-2 peptide, or fragment thereof, is detected.

Preferably, the at least one HOX peptide is selected from any HOX peptide as listed below, provided that the HOX peptide, or a fragment thereof, is detectable in a body fluid such as serum or urine.

Preferably, the at least one HOX peptide, or a fragment thereof is from the HOXA, the HOXB, the HOXC or the HOXD subfamily. If more than one HOX peptide is used, then these may be from the same family or from a combination of families. Combinations of fragments are also envisaged, either fragments of the same protein or fragments of different proteins. Combinations of different peptides can provide more accurate diagnoses. It is preferred that the HOX peptide is not HOXA4, HOXA1, HOXA7, HOXB3, or HOXB9.

It is particularly preferred that the HOX peptide is the HOXC4 peptide, and/or the HOXB6 peptide and/or the HOXB5 peptide, and/or the HOXA3 peptide, and/or the HOXD9 peptide or fragments thereof.

Preferably, the HOXC4 peptide is that provided in Sequence ID NO. 1 (NCBI accession no. P09017, gi:123279), or a fragment thereof. Preferably, the HOXB6 peptide is that provided in Sequence ID NO. 2 (NCBI accession no. P17509, gi:116242515), or a fragment thereof. Preferably, the HOXB5 peptide is that provided in Sequence ID NO. 3 (NCBI accession no. P09067, gi:400000), or a fragment thereof. Preferably, the EN-2 peptide is that provided in Sequence ID NO. 4 (NCBI accession no. P19622, gi:21903415) or a fragment thereof. Preferably, the HOXA3 peptide is that provided in Sequence ID NO.5 (mRNA NCBI accession no. NM_030661, gi: 84043946), or a fragment thereof. Preferably, the HOXD9 peptide is that provided in Sequence ID NO.6 (mRNA NCBI accession no. NM_014213, gi: 23397673), or a fragment thereof.

While reference is made to HOXC4, the HOXC4 peptide or a fragment thereof, it will be understood that these terms can be used interchangeably, unless otherwise apparent. The same follows for other HOX peptides and EN-2.

Furthermore, where reference is made herein to HOXC4, HOXB6, HOXB5, HOXA3 or HOXD9, this also applies to other HOX peptides, or combinations thereof, unless otherwise apparent.

Similarly, where reference is made herein to a particular sequence, such as a reference sequence or a Sequence ID NO, this applies to all Sequence ID NOs. and any of the HOX sequences provided below, unless otherwise apparent.

Preferably, the fragment comprises at least 80% sequence homology to the reference sequence (e.g. HOXC4, HOXB6, HOXB5, HOXA3, HOXD9 or EN-2), more preferably 85%, more preferably 90%, more preferably 95%, more preferably 97%, more preferably 99% and most preferably 99.9% sequence homology to the reference sequence, or as close thereto as appropriate. Suitable methods for establishing sequence homology include the BLAST programme.

Preferably, the fragment comprises at least 80% sequence identity to the reference sequence (e.g. HOXC4, HOXB6, HOXB5, HOXA3, HOXD9 or EN-2), more preferably 85%, more preferably 90%, more preferably 95%, more preferably 97%, more preferably 99% and most preferably 99.9% sequence identity to the reference sequence, or as close thereto as appropriate. Suitable methods for establishing sequence identity include the BLAST programme.

Two polypeptides are said to be "homologous", as the term is used herein, if the sequence of one of the polypeptides has a high enough degree of identity or similarity to the sequence of the other polypeptide. "Identity" indicates that at any particular position in the aligned sequences, the amino acid residue is identical between the sequences. "Similarity" indicates that, at any particular position in the aligned sequences, the amino acid residue is of a similar type between the sequences. Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). Percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1].

Preferably, the fragment comprises at least four consecutive amino acids from the reference sequence, more preferably at least 5, more preferably at least 6, more preferably at least 7, more preferably at least 8 consecutive amino acids from the reference sequence, such as Sequence ID NO. 1, 2, 3, 4, 5 or 6, although longer fragments at least 10, 15, 20, 25, 30, 50, 75, 100, 150, 200, 225 and up to at least 250 amino acids are also preferred. Fragments also include truncated peptides that have x amino acids deleted from the N-terminus and/or C-terminus. In such truncations, x may be 1 or more (ie. 1, 2, 3, 4, 5, 6, 7, 8, 9, 10, 15, 20, 30, 40, 50, 60, 70, 80, 90, 100 or more), but preferably less than 150.

Without being bound by theory, it is thought that HOXC4 is secreted via a non-classical route, with no signal sequence required. The sequence given in Sequence ID NO. 1 is, therefore, thought to be the same as the protein found in serum. This is corroborated by the observation that the detected band is of a corresponding size (Mw) to the predicted size based on the gene sequence. HOX proteins may also leave cells through other mechanisms e.g. cell lysis.

The term "biomarker" is used throughout the art and means a distinctive biological or biologically-derived indicator of a process, event or condition. In other words, a biomarker is indicative of a certain biological state, such as the presence of cancerous tissue. In some cases, different forms of biomarkers can be indicative of certain disease states but, without being bound by theory, it is thought that merely the presence of elevated levels of a HOXC4 peptide, or fragment thereof, in body fluids such as serum, is indicative of prostate cancer. Although it is not currently envisaged that different glycoforms, for instance, of the HOXC4 peptide, are secreted, these are nevertheless encompassed by the present invention. For instance, different glycoforms, such as altered glycoform structure or sugar content, may yet be determined for HOXC4, but these are encompassed and may even also be indicative of the progress of the prostate cancer. Truncations, mutations, or deletions of, or ligations to, the HOXC4 peptide, or fragment thereof, are also envisaged.

However, the principal discovery underpinning the present invention is that there is a significant increase in the level of HOXC4 detectable in body fluids, such as the serum. It is thought that HOXC4 is secreted, but it is also envisaged that it may be due to HOXC4 protein leaking out of dying cells. Similarly, EN-2 may be secreted or may be detectable in body fluids due to leaking from damaged or dead cells. Such increased levels are indicative of both early stage and late stage prostate cancer. Whilst there is a significant rise between control or normal levels and early stage prostate cancer, there is also a very significant increase between early and late stage prostate cancer. Broadly, it is an advantage of the present invention that the substance and also the state of the prostate cancer can be detected. This aids in the prognosis and provision of suitable therapies.

It is also an advantage of the present invention that it is able to distinguish over conditions such as benign prostatic hyperplasia BTH (BPH). Such conditions, which lead to an enlargement of the prostatic gland, can be misinterpreted as prostate cancer using established techniques for determining the presence of prostate cancer, such as Digital Rectal Examination (DRE). It is another advantage of the present invention that an accurate diagnosis can be provided without resorting to unpleasant and potentially harmful invasive procedures, which may also be inaccurate. Furthermore, the present invention is particularly sensitive. Preferably the methods of the present invention may detect the onset of prostate cancer prior to any other detection method and prior to the onset of the overt symptoms of prostate cancer. Thus, the cancer may be treated at an early stage when it is more susceptible to such treatment and less likely to have entered the metastatic stage.

Different types of prostate cancer are known. The most common starts in the prostate gland cells and is known as prostate adenocarcinoma. However, other forms of prostate cancer exist, such as, sarcomas, small cell carcinomas, and transitional cell carcinomas. The methods of the invention may be used to detect the onset of any of these types of cancer, although the detection of adenocarcinoma is preferred.

The progression of cancer is monitored by a staging process. This indicates how well developed the cancer is and if it has spread. The score runs from one to four, with the prognosis becoming progressively worse at each stage.

Stage One: Malignant cells are confined to the prostate; they have not spread to the lymph nodes or other organs; Gleason scores are between two to four, and less than five percent of the prostate is composed of tumor growth.

Stage Two: Gleason scores are five or higher, or over five percent of the gland shows abnormal growth; the cancer is still restricted to the prostate.

Stage Three: Malignant cells have spread to the seminal vesicles, but not to the lymph nodes or other organs.

Stage Four: The lymph nodes, pelvic tissue or more distant organs are affected.

Preferably, the methods of the invention detect the onset of prostate cancer prior to, or during stage one or stage two, more preferably stage one.

The peptide biomarkers of the present invention can be used in methods of diagnosis, for instance clinical screening, and in methods of prognosis assessment, monitoring the results of therapy, identifying patients most likely to respond to a particular therapeutic treatment, drug screening and development. Furthermore, the biomarkers of the present invention and uses thereof are valuable for identification of new drug treatments and for discovery of new targets for drug treatment.

Thus, in a further aspect, the invention provides a method of diagnosing or monitoring the progression of prostate cancer, comprising detecting and/or quantifying at least one homeodomain-containing transcription factor such as a HOX peptide or EN-2 peptide or a fragment thereof. Preferably, the peptide comprises or consists of the amino acid sequence according to SEQ ID NO 1, 2, 3, 4, 5 or 6. Preferably the at least one HOX peptide, the EN-2 peptide, or a fragment thereof, is present in a biological sample from a test subject. Said biological sample preferably being a body fluid sample.

The body fluid may be any human body fluid, including cellular fluid, cerebrospinal fluid (CSF), semen, urine, blood, lymph or saliva. However, it is particularly preferred that the body fluid is whole blood, in particular blood serum, or urine. It is also preferred that the body fluid is substantially or completely free of whole/intact cells. Preferably the body fluid is free of platelets and cell debris (such as that produced upon the lysis of cells). Preferably the body fluid is free of both prokaryotic and eukaryotic cells.

Such fluids can be obtained by any number of means known in the art, such as will be apparent to the skilled person. For instance, a urine sample is easily attainable, whilst blood or serum samples can be obtained parenterally by using a needle and syringe, for instance. Cell free or substantially cell free samples can be obtained by subjecting the body fluid to various techniques known to those of skill in the art which include, but are not limited to, centrifugation and filtration.

Although it is generally preferred that no invasive techniques are used to obtain the sample, it still may be preferable to obtain samples such as tissue homogenates, tissue sections and biopsy specimens.

Monitoring methods of the present invention can be used to detect the onset, progression, stabilisation, amelioration and/or remission of prostate cancer. Thus, the detection of the at least one HOX peptide, EN-2 peptide or a fragment thereof, can be used to determine the progression of the disease, in order to direct a physician towards a particular treatment.

Preferably, at least two detection and/or quantification steps are provided, preferably spaced apart temporally, for instance by a few days, weeks, years or, more preferably, months, to determine whether the levels of the at least one HOX or EN-2 peptide, or a fragment thereof, have changed, thus indicating whether there has been a change in the progression of the cancer. This enables comparisons to be made between a level of the biomarker in samples taken on two or more occasions, as an increase in the level of the peptide over time is indicative of the onset or progression of the cancer, whereas a decrease in the level of the peptide may indicate amelioration and/or remission of the cancer.

Preferably, a method of diagnosis or of monitoring according to the present invention comprises comparing the level of the peptide present in a test sample, with the level in one or more controls. Preferably, the controls may be from the same patient from a previous sample, to thus monitor onset or progression. However, it is also preferred that the controls may be normalised for a population, particularly a healthy or normal population, where there is no prostate cancer. In other words, the control may consist of the level of a biomarker found in a normal control sample from a normal subject.

Thus, there is provided a method of diagnosing prostate cancer comprising quantifying or detecting the amount of at least one HOX peptide, the EN-2 peptide or a fragment thereof, and comparing the amount of said peptide in said test sample with the amount present in a normal control biological sample from a normal subject or from the same subject well prior to the incidence of disease. If a significant increase in the level of the at least one HOX peptide, the EN-2 peptide or a fragment thereof, is found in the test sample, then it is indicative that the disease is either progressing or has initiated.

As noted above, this method of detection of at least one HOX peptide, the EN-2 peptide or a fragment thereof is particularly useful in detecting early stage prostate cancer and is more sensitive than the traditional test of detecting PSA levels. Thus, the methods of the invention are particularly useful for confirming cancer when a patient has tested negative for cancer using conventional methods, such as the detection of PSA.

In general, the level of the at least one HOX peptide or EN-2 peptide secretion into the body fluids is in the ranges described below.

It will be understood that the terms "peptide" and "protein" are interchangeable as used herein, unless otherwise apparent.

Table 1 and FIG. 1, for instance, show a very sizeable increase in HOXC4 serum protein concentrations. Table 2 and FIG. 2 show similar results for HOXB6. We have also shown that HOXB6 is a biomarker for late-stage prostate cancer (data not shown). HOXB5 is also a biomarker, but is less preferred than HOXB6 or HOXC4 (Table 3 and FIG. 7). Other alternative biomarkers include HOXA3 and HOXD9 (see FIG. 8).

Preferably, the increase is statistically significant, determined by using standard methods, such as a "t-test" providing confidence intervals of preferably at least 80%, more preferably at least 85%, more preferably at least 90%, more preferably at least 95%, more preferably at least 97%, more preferably at least 99%, more preferably at least 99.5%, more preferably at least 99.95%, and most preferably at least 99.99%.

Preferably, the increase between the control and a sample indicative of early stage prostate cancer is around between 110-200%, more preferably around between 120-180%, more preferably around between 130-160%, more preferably around between 140-150%, more preferably around between 110-140%, more preferably around between 115-130%, more preferably around between 120-130%, more preferably around between 120-140%, and most preferably around 125%. Other combinations of the above end points are also envisaged.

With regard to determining late stage or advanced cancer, the increase between the control and a sample indicative of said late stage prostate cancer is around between 400-800%, more preferably around between 450-750%, more preferably around between 500-700%, more preferably around between 520-680%, more preferably around between 540-640%, more preferably around between 550-620%, more preferably around between 560-600%, more preferably around between 570-590%, and most preferably around 580%. The increase may also be in the range 550-800% or 400-600%. Other combinations of the above end points are also envisaged.

An increase between early and late stage cancer may be measured relative to a normal (i.e. cancer free) control or to an early stage sample or control in the same patient. Relative to an early stage sample an increase of around between 100% and 300%, more preferably around between 150% and 250%, more preferably around between 175% and 225%, more preferably around between 185% and 215%, more preferably around between 100% and 220%, more preferably around between 170% and 300%, and most preferably around 200% is preferred.

As mentioned above, where reference is made herein to at least one homeodomain-containing peptide, this applies to HOX peptides, such as HOXC4, HOXB6, HOXB5, HOXA3 and HOXD9, and to the EN-2 peptide, unless otherwise apparent.

Where reference is made herein to at least one HOX peptide or HOX peptides, this applies to HOXC4, HOXB6, HOXB5, HOXA3 and HOXD9, in particular as well as the other HOX peptides listed below, unless otherwise apparent.

In terms of absolute amounts of at least one HOX or EN-2 protein per ml of body fluid, preferably serum, this is preferably around between 0.5-1.5 ng/ml, more preferably around between around between 0.75-1.25 ng/ml, and most preferably around 1.0 ng/ml for control samples. For early stage cancer samples, preferred ranges are around between 2.0-5.0 ng/ml, more preferably around between 2.5-4.5 ng/ml, more preferably around between 2.5-4.0 ng/ml, more preferably around between 2.75-3.5 ng/ml, more preferably around between 2.75-3.0 ng/ml, more preferably around between 2.0-3.5 ng/ml, more preferably around between 2.0-3.0 ng/ml, and most preferably around 3.0 ng/ml.

For late stage cancer samples, preferred ranges are around between 6.0-20 ng/ml, more preferably around between 8.0-15 ng/ml, more preferably around between 8.5-13 ng/ml, more preferably around between 9.0-12 ng/ml, more preferably around between 9.5-11 ng/ml, more preferably around between 7-13 ng/ml, more preferably around between 8.5-16 ng/ml, and most preferably around 10 ng/ml.

The term "diagnosis" encompasses identification, confirmation, and or characterisation of the presence or absence of prostate cancer, together with the developmental stage thereof, such as early stage or late stage, or benign or metastatic prostate cancer.

It will be appreciated that the "early stage" and "late stage" nature of the cancer disease states can be determined by a physician. It is also envisaged that they can refer to non-metastatic and metastatic, respectively.

The invention also provides a method of monitoring the efficacy of a treatment for prostate cancer, comprising detecting and/or quantifying the at least one HOX peptide, EN-2 peptide, or a fragment thereof, present in a biological sample from a subject. As above, it may be preferable to obtain two samples, separated temporally by, for instance, a couple of months, in order to determine whether there has been any progress in the treatment, in other words, if the levels of at least one HOX peptide, EN-2 peptide, or a fragment thereof, have increased or decreased. A decrease in the levels of said at least one HOX peptide or EN-2 peptide indicates that the disease is regressing and thus the treatment regime is successful. Such a monitoring of a disease will quickly show whether a patient is responding to a treatment or is refractive to a treatment. If the latter, then an alternative treatment may be provided. Such a method therefore provides a fast indication of whether a treatment regime is effective and allows the physician to alter such a regime until an effect is observed in the patient.

In the method of the present invention, it is preferred that the amount of the peptide, or a fragment thereof, in a test sample is compared with the amount present in one or more control(s) and/or one or more previous test sample(s) taken at an earlier time from said same test subject. The length of time between the earlier and later samples may be only a few days, but may be up to several months or even several years, and will be determined by the physician, based on the progression of the disease and the patient's medical history. Alternatively, the control may be a test sample from a disease-free patient.

The peptide, or a fragment thereof, is detected by confirming the presence of said biomarker. Quantifying the amount of the biomarker present in a sample preferably includes determining the concentration of the peptide biomarker in the sample. The detecting and/or quantifying steps can be performed directly on the sample, or indirectly on an extract therefrom, or a dilution thereof.

The present invention relates to biomarkers and it will be appreciated that these have to be detectable in the body fluid. Some members of the HOX family may not be detectable in body fluid and are, therefore not biomarkers according to the present invention.

Detectable levels of the at least one HOX peptide, the EN-2 peptide or fragments thereof are discussed elsewhere, but it will be appreciated that there may be a number of reasons why a HOX peptide, the EN-2 peptide or fragments thereof are not detectable. Without being bound by theory, one reason may be that the peptide is degraded in the body fluid, i.e. is not "stable."

Thus, it is preferred that the at least one HOX peptide, the EN-2 peptide or fragments thereof are substantially not degraded and/or are still detectable (i.e. present at detectable concentrations) at the body periphery, i.e. a vein near the surface of the skin, preferably the arm, where it can be more simply sampled.

The peptide may be released into the body fluid, either by cell break-up or leakage, or by secretion.

Detection and/or quantification of the at least one HOX peptide or the EN-2 peptide, or fragments thereof may be by any method suitable to detect the presence and/or amount of a specific protein or peptide in a biological sample. This may be by direct detection of the biomarker, by instance by MALDI-TOF or SELDI.

However, it is also preferred that the at least one HOX peptide or EN-2 peptide, or fragment thereof, is detected directly or indirectly via interaction with a ligand or ligands. Such ligands may include an anti-HOX or anti-EN-2 antibody or a binding fragment thereof, an aptamer, or an oligonucleotide. It will be appreciated that these ligands must be capable of specifically binding the HOX peptide or EN-2 peptide, or a fragment thereof. It may be suitably labelled and comprise an affinity tag. Suitable labels may be fluorescent, radioactive or luminescent. The labels may be attached to the antibody directly, or via a linker.

For example, detecting and/or quantifying may be performed by one or more methods selected from the group consisting of: MALDI-TOF, SELDI, 1-D or 2-D gel-based analysis systems, Liquid Chromatography combine liquid chromatography and Mass spectrometry techniques. The latter of these may include, preferably, ICAT®, or iTRAQ® (both available from Applied Biosystems, USA).

Liquid chromatographic techniques may include HPLC (high pressure liquid chromatography) or even low pressure liquid chromatography (LPLC). Furthermore, methods such as thin-layer chromatography, NMR spectroscopy and any other method described herein, are also preferred.

The peptide, or a fragment thereof, may be detected and/or quantified using immunological methods, such as sandwich immunoassays, for instance an enzyme linked immunosorbent assay (ELISA), radio-immunoassays (RAI), enzyme immunoassays (ETA), Western Blotting, immunoprecipitation. Also preferred are particle-based immunoassays, which may include, for instance, using gold, silver, or latex particles, magnetic particles or Q-dots. Such methods may be performed, for example, in microtitre plate or strip format or on a "chip".

Particularly preferred are ELISAs comprising antibodies specific for the at least one HOX or EN-2 peptide. The anti-HOX or anti-EN-2 antibody or antibodies are preferably linked, either directly or via a linker, to a reporter molecule, such as a radioisotope, a fluorescent molecule, a luminescent molecule or an enzyme. One example of a preferred enzyme is alkaline phosphatase, available from Invitrogen, UK, although other reporters are known in the art.

An example of anti-human HOXC4 antibody is available from Abcam, UK, Catalogue No. ab24338. This is rabbit anti-human HOXC4 antibody and, therefore, it may be preferable to use a secondary, anti-rabbit IgG antibody linked to a reporter, such as alkaline phosphatase, to detect the HOXC4 antibody-complex. An example of an anti-HOXB6 antibody is from Abcam, cat no. ab26077. An example of an anti-HOXB5 antibody is from Abcam, cat no. ab26079. An example of an anti-HOXA3 antibody is from Abcam, cat no. ab28771. An example of an anti-HOXD9 antibody is from Abcam, cat no. ab60708. Examples of other anti-HOX antibodies are known. An example of an anti-EN-2 antibody is from Abcam, cat no. ab45867.

Western blotting methods are also preferred, particularly as these can provide densitometry data.

Suitable comparative levels of the presence of the at least one HOX or EN-2 peptide sufficient to distinguish between the control, early-stage and late-stage cancers, or combinations thereof, are discussed above.

Where antibodies are used, these may be polyclonal, monoclonal, bispecific, humanised or chimeric antibodies. The antibodies may consist of a single chain but would preferably consist of at least a light chain or a heavy chain but it will be appreciated that at least one Complementarity Determining Region (CDR) is required in order to bind a HOX epitope or an EN-2 epotope.

Of course, it will also be appreciated that the epitope or epitopes must be available for binding or recognition by the ligand, such as an antibody. Anti-HOX and anti-EN-2 antibodies are already known, but if further antibodies or binding ligands, with different specificities are required then these could be obtained. Methods of making antibodies are known in the art. For example, if polyclonal antibodies are desired, then a selected mammal, such as a mouse, rabbit, goat or horse may be immunised with the antigen of choice, such as human HOX or EN-2. The serum from the immunised animal is then collected and treated to obtain the antibody, for instance by immunoaffinity chromatography. Human HOX or EN-2 could, for instance, be injected into rabbits triggering a rabbit immune response, raising anti-HOX or anti-EN-2 antibodies, which can thereby be isolated, using standard methods.

Of course, monoclonal antibodies could be produced by methods known in the art, and are generally preferred. The general methodology for making monoclonal antibodies using hybridoma technology is well known (see, for example, Kohler, G. and Milstein, C., Nature 256: 495-497 (1975);

Kozbor et al., Immunology Today 4: 72 (1983); Cole et al., 77-96 in Monoclonal Antibodies and Cancer Therapy, Alan R. Liss, Inc. (1985).

Therefore, an antibody, as referred to herein, must consist of an epitope-binding region, such as CDR. As used herein, the term "antibody" refers to intact molecules as well as to fragments thereof, such as Fab, Fab', F(ab')$_2$ and Fv, which are capable to binding to an epitope. Preferably, the antibody also comprises an effector portion, such as the Fc region.

The antibody may of any suitable class, including IgE, IgM, IgD, IgA and, in particular, IgG. The various subclasses of these antibodies are also envisaged.

Thus, it is also preferred that a biosensor is used to detect the at least one peptide biomarker, or a fragment thereof. The biosensor may incorporate an immunological method, as described above, for instance, for detection of the biomarker, or electrical, thermal, magnetic, optical for instance a hologram, or acoustic means or technologies. Using such biosensors, it is envisaged that the biomarker is detected and/or quantified. Thus, in a further aspect, the present invention provides the use of a biosensor to detect and/or quantify the peptide, or a fragment thereof.

Preferably, the at least one HOX or EN-2 biomarker can be detected using a biosensor based on the use of "smart" holograms, or high frequency acoustic systems, particularly as such systems are amenable to array configurations. For instance, with smart hologram sensors, available from Smart Holograms Limited, Cambridge UK, a holographic image is stored in a thin polymer film that is sensitised to react specifically with the biomarker. On exposure, the biomarker reacts with the polymer leading to an alteration in the image displayed by the hologram. The test result readout can see a change in the optical brightness, image, colour and/or position of the image. This can even be read by eye.

It will be appreciated that it is preferred that the biosensors capable of detecting and/or quantifying the at least one HOX or EN-2 biomarker, combine biomolecular recognition with appropriate means to convert detection of the presence, or quantification, of said biomarker in a sample into a detectible signal. For instance, imprinted recognition elements, thin film transistor technology, magnetic acoustic resonator devices and other novel acousto-electrical systems may preferably be employed in the present biosensor for detection and/or quantification of the at least one HOX or EN-2 biomarker. Preferably, a biosensor according to the invention will detect one or more of, preferably two, three, four, five or all six of, HOXC4, HOXB5, HOXB6, HOXA3, HOXD9 and EN-2. Further preferred biosensors may also further detect other HOX biomarkers as referred to above.

Preferably, the biosensor includes a ligand and/or an antibody, as discussed above. The biosensor may be provided on a suitable array or "chip", such that the biosensor is capable of specific binding to the at least one HOX peptide, or EN-2 peptide, or a fragment thereof, a detection means is provided. Suitable detection means are discussed above, but may include reporter systems, such as alkaline phosphatase, or smart holograms, capable of providing a detectible signal to the user to indicate that specific binding of the at least one HOX or EN-2 peptide, or a fragment thereof, has been achieved and, preferably, an indication of the concentration of HOX or EN-2 or the number of specific binding events that have occurred on said array or chip.

The present invention further provides kits for said detection and/or quantification. Such kits are useful in the diagnosis and/or monitoring of prostate cancer. Thus, such kits will preferably comprise a biosensor such as a ligand, preferably an antibody, capable of specifically binding at least one peptide, or a fragment thereof, and means for indicating said specific binding for the user, for instance using a reporter system as described herein. Particularly referred kits include an array or a chip.

In a further aspect, the invention provides the use of a biosensor, preferably a ligand and most preferably an antibody, capable of specific binding and recognition of at least one HOX or EN-2 peptide, or a fragment thereof, to identify a substance capable of suppressing the generation of the at least one HOX or EN-2 peptide, or a fragment thereof. Preferably, this substance is capable of suppressing the production of the biomarker by the prostate cancer. In other words, the ligand may be used to determine the efficacy or otherwise of a putative or established anti-prostate cancer treatment.

Thus, a method for detecting the efficacy of a putative anti-cancer treatment may include the steps of:

(a) incubating a whole cell expressing a HOX peptide or an EN-2 peptide and detecting the amount of HOX peptide or an EN-2 peptide released, (b) treating the cell with a putative anti-cancer treatment, (c) detecting the amount of HOX peptide or an EN-2 peptide released following treatment, and (d) comparing the amount of HOX peptide or an EN-2 peptide released both before and after treatment to see whether the putative anti-cancer treatment has an effect on the amount of peptide released.

Alternatively, a method may comprise the steps of:

(a) incubating a labelled ligand with a whole cell expressing a HOX peptide or an EN-2 peptide on the cell surface, or a cell membrane containing a HOX peptide or an EN-2 peptide, (b) measuring the amount of labelled ligand bound to the whole cell or the cell membrane;

(c) adding a putative anti-cancer agent to a mixture of labelled ligand and the whole cell or the cell membrane of step (a) and allowing the mixture to attain equilibrium;

(d) measuring the amount of labelled ligand bound to the whole cell or the cell membrane after step (c); and (e) comparing the difference in the labelled ligand bound in step (b) and (d), such that the compound which causes the reduction in binding in step (d) is considered to be an inhibitor of HOX or EN-2 expression and therefore an anti-cancer agent.

For example, a cell line such as the prostate carcinoma cell line LNCaP could be used in such an assay. The LNCaP cells could be grown in the presence or absence of a putative or established anti-cancer agent, and the relative expression of EN-2 compared. A lower expression level of EN-2 would indicate a better anti-cancer activity. The expression levels could be detected by detecting the protein produced (i.e. the final product) or by detecting the RNA produced (i.e. an intermediate product). Methods of detecting the protein product are discussed above. The RNA may be detected using, for example, quantitative PCR or an oligonucleotide array.

The above also relates to the methods and kits of the present invention.

Other methods or kits for use in accordance with the present invention, will be apparent to the skilled person. These may include, for instance, biomarker detection systems are disclosed in US-2006-014301, US-2004-063216, WO 01/92879 and WO 02/054936.

Thus, the present invention can be used to identify new anti-prostate cancer treatments, wherein the levels of at least one HOX or EN-2 peptide, or a fragment thereof, are detected and/or quantified in the presence or absence of the putative anti-cancer agent, in order to determine the efficacy thereof.

The present invention can also be used in a method of high-throughput screening technologies, for instance in a configured array format, such as on a chip or in a multiwell array.

As prostate cancer is a male-related disease, it will be appreciated that the subject or patient is a male.

EXAMPLE 1

HOXC4

Figure 1:
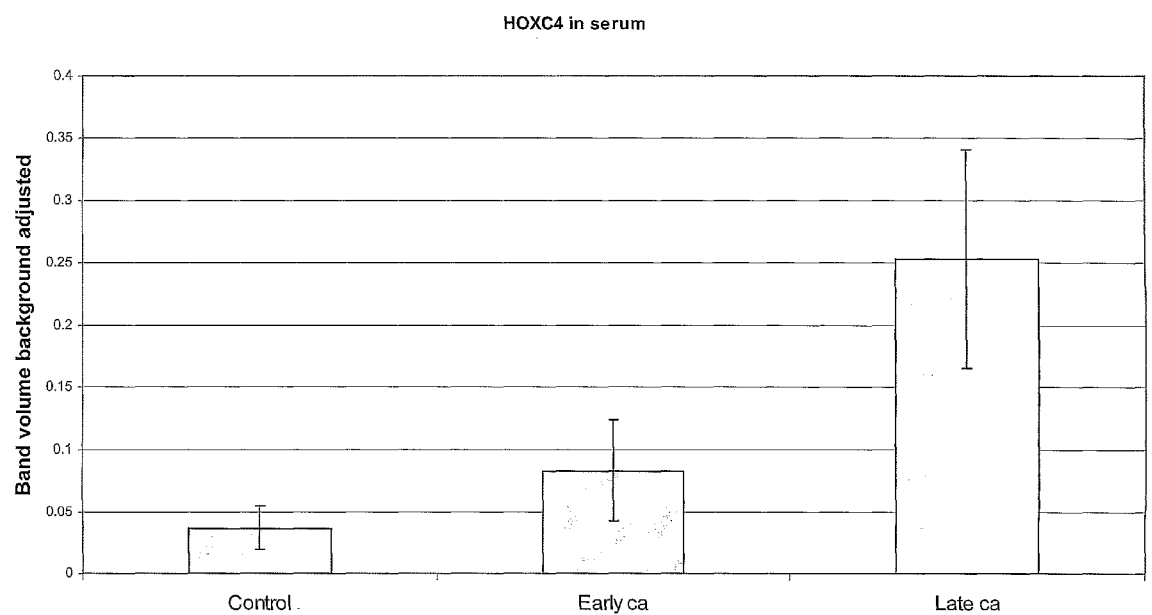
FIG. 1: An example of a western blot looking for HOXC4 protein in serum. The results were also analysed by densitometry, and are shown as the mean of all six samples from each group. Error bars show the standard error of the mean. These data indicate that HOXC4 is potentially a specific and accurate diagnostic marker for prostate cancer at both early and late stages of the disease.

Serum was obtained from six patients with advanced, hormone-refractory prostate cancer, six patients with early stage prostate cancer where tumours are small and confined to the prostate, and from six age-matched controls. This was desalted and fractionated using a 12.5% PAGE/SDS gel. Human HOXC4 protein (UniProtKB/Swiss-Prot entry number P09017) was detected using western blotting with a rabbit anti-human HOXC4 antibody (Abcam, UK, catalogue number ab24338), together with a secondary anti-rabbit IgG antibody linked to alkaline phosphatase (Invitrogen, UK). Using this method, we detected high levels of HOXC4 protein in the serum of all the prostate cancer patients, but only very low levels in age-matched control serum (FIG. 1).

The results are shown below in Table 1.

HOXC4 could be used as the basis of a diagnostic and/or prognostic test for prostate cancer by using a standard assay technique such as ELISA. This would involve the use of an anti-HOXC4 antibody linked to a reporter such as alkaline phosphatase in order to quantify the amount of HOXC4 protein in patient serum samples. Other methodologies could also be used, including western blotting. The amount of HOXC4 protein would provide an indication as to whether the disease is present and what stage it has reached.

TABLE 1

| Gel name: HoxC4 blot 131006 (Raw 1-D Image) | | | | | | |
|---|---|---|---|---|---|---|
| Index | Name | Patient | Diagnosis | Volume OD * mm2 | Adj. Vol. OD * mm2 | % Adj. Vol. |
| 1 | U1 | HR29 | Cancer | 6.844796 | 0.272431 | 24.320686 |
| 2 | U2 | HR28 | Cancer | 6.460027 | 0.092836 | 8.2877258 |
| 3 | U3 | HR27 | Cancer | 9.731784 | 0.393355 | 35.115964 |
| 4 | U4 | SR5 | Early cancer | 6.108735 | 0.086538 | 7.7255409 |
| 5 | U5 | SR2 | Early cancer | 6.26387 | 0.01121 | 1.0007083 |
| 6 | U6 | SR1 | Early cancer | 8.427193 | 0.15222 | 13.589161 |
| 7 | U7 | VR30 | Healthy | 6.459172 | 0.045458 | 4.0581642 |
| 8 | U8 | VR23 | Healthy | 9.760506 | 0.062926 | 5.6175665 |
| 9 | U9 | VR21 | Healthy | 6.740683 | 0.003187 | 0.2844833 |
| | | | Mean values | sd | sem | % increase |
| Control | | | 0.037190112 | 0.030716 | 0.0177548 | 0 |
| Early cancer | | | 0.08332277 | 0.07056 | 0.0407864 | 124.0455 |
| Late cancer | | | 0.252873795 | 0.151211 | 0.0874053 | 579.949 |

NB. Probed membranes with primary antibody for 1 hour only

```
SEQ ID NO. 1:
HOXC4 NCBI Accession # P09017
   1 MIMSSYLMDS NYIDPKFPPC EEYSQNSYIP EHSPEYYGRT RESGFQHHHQ ELYPPPPPRP

61 SYPERQYSCT SLQGPGNSRG HGPAQAGHHH PEKSQSLCEP APLSGASASP SPAPPACSQP

121 APDHPSSAAS KQPIVYPWMK KIHVSTVNPN YNGGEPKRSR AAYTRQQVLE LEKEFHYNRY

181 LTRRRRIEIA HSLCLSERQI KIWFQNRRMK WKKDHRLPNT KVRSAPPAGA APSTLSAATP

241 GTSEDHSQSA TPPEQQRAED ITRL
```

EXAMPLE 2
HOXB6

The detection of HOXB6 in these samples was done exactly as for HOXC4 except that the primary antibody was rabbit-anti human HOXB6 (from Abcam, cat no. ab26077). The relative values for HOXB6 protein were assessed by densitometry of the X-ray film (using the bands located at its predicted molecular weight). These values are the optical density of the band relative to that of the local background. Therefore, it will be appreciated that a negative comparative densitometry value is possible, as shown for the Age Matched Controls (AMCs), although it will be appreciated that this does not translate to a negative amount of HOXB6 protein.

Figure 2:
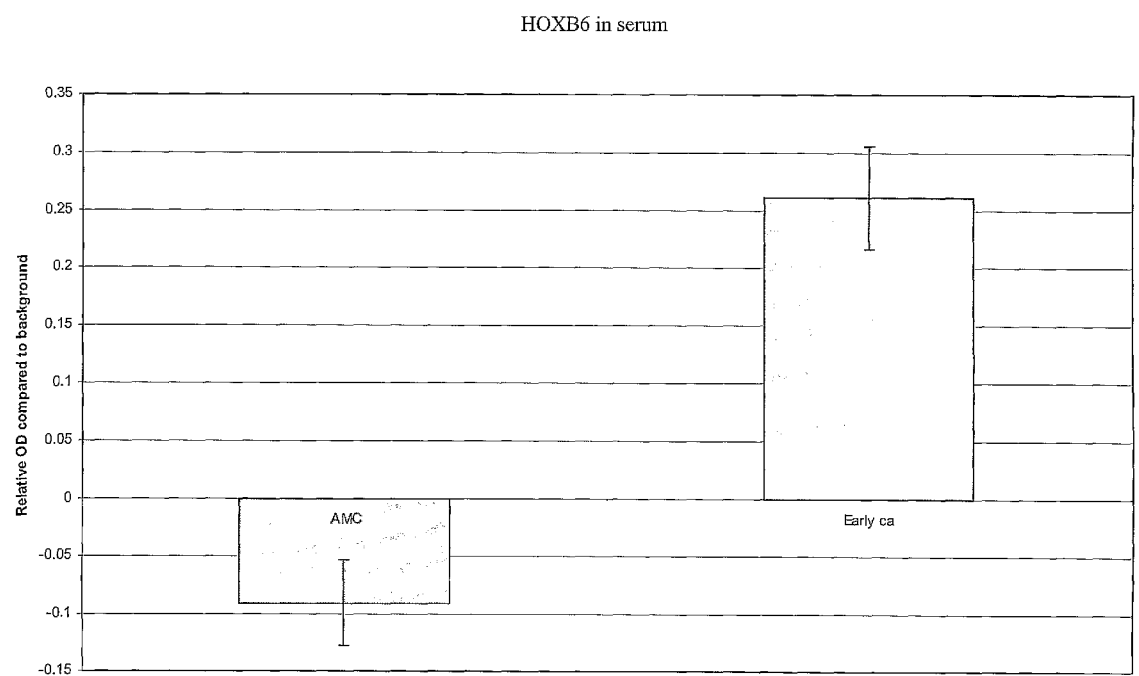
FIG. 2: Detection of HOXB6 in six patients with early stage prostate cancer where tumours are small and confined to the prostate, and from six age-matched controls.

These data are shown graphically in FIG. 2.

TABLE 2

HOXB6 in serum
Values are relative optical density of bands

| | | |
|---|---|---|
| AMC1 | | −0.02671 |
| AMC2 | | −0.08899 |
| AMC3 | | −0.15478 |
| Early1 | | 0.182775 |
| Early2 | | 0.33511 |
| Early3 | | 0.265214 |

| | mean | sd | sem |
|---|---|---|---|
| AMC | −0.09016 | 0.064043 | 0.036977 |
| Early cancer | 0.261033 | 0.076253 | 0.044026 |

```
SEQ ID NO. 2:
HOXB6 NCBI Accession # P17509
    1 MSSYFVNSTF PVTLASGQES FLGQLPLYSS GYADPLRHYP APYGPGPGQD KGFATSSYYP

61 PAGGGYGRAA PCDYGPAPAF YREKESACAL SGADEQPPFH PEPRKSDCAQ DKSVFGETEE

121 QKCSTPVYPW MQRMNSCNSS SFGPSGRRGR QTYTRYQTLE LEKEFHYNRY LTRRRRIEIA

181 HALCLTERQI KIWFQNRRMK WKKESKLLSA SQLSAEEEEE KQAE
```

EXAMPLE 3
EN-2

Figure 3:
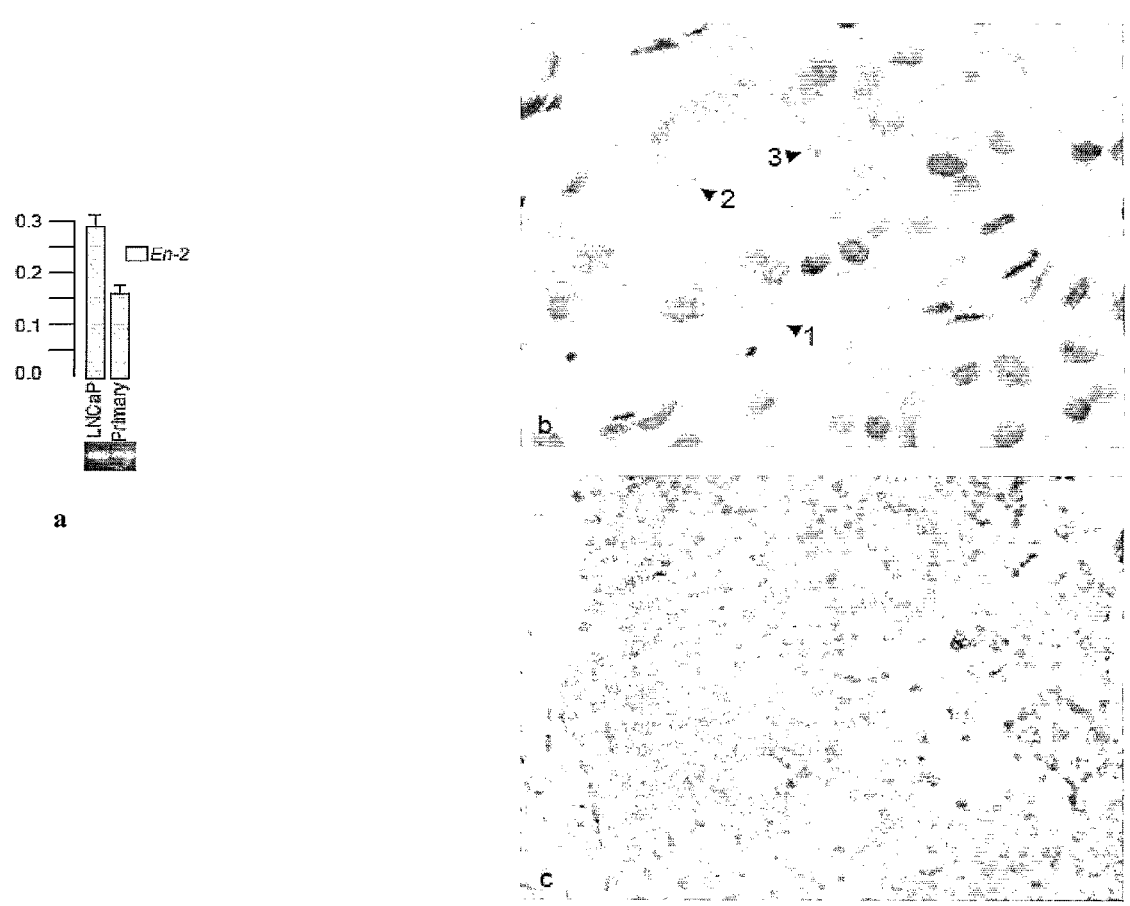
FIG. 3: (a) RT-QPCR analysis of EN-2 expression in LNCaP and primary tumour cells (transcript level as a proportion of β-actin). (b,c) Core biopsy of a prostatic adenocarcinoma stained with anti-En2 antibody. En2 positive staining (brown) is present in the cytoplasm of tumour cells, with strongest staining at the luminal border (1). En2 positive blebs are visible attached to the luminal border (2) or free within the lumen (3). The nuclei are stained blue. Magnification: (a) ×100, (b) ×60.

Using quantitative PCR (QPCR) the expression levels of EN-2 were tested in the human prostate carcinoma cell line LNCaP (Horoszewicz et al., 1983). This is a cell line derived from a metastatic lesion of a human prostate adenocarcinoma, and is widely used as an in vitro model of this cancer. Furthermore the expression of EN-2 was tested in tissue obtained from biopsies of prostate tumours. Both samples expressed EN-2. The primary tumour cells also expressed EN-2 as protein. This could be detected in sections of prostatic adenocarcinomas (FIG. 3a). EN-2 staining in these sections is present in both the cytoplasmic and nuclear compartments but is most intense at the luminal borders and in secretory blebs entering the lumen (FIG. 3b,c).

Figure 4:
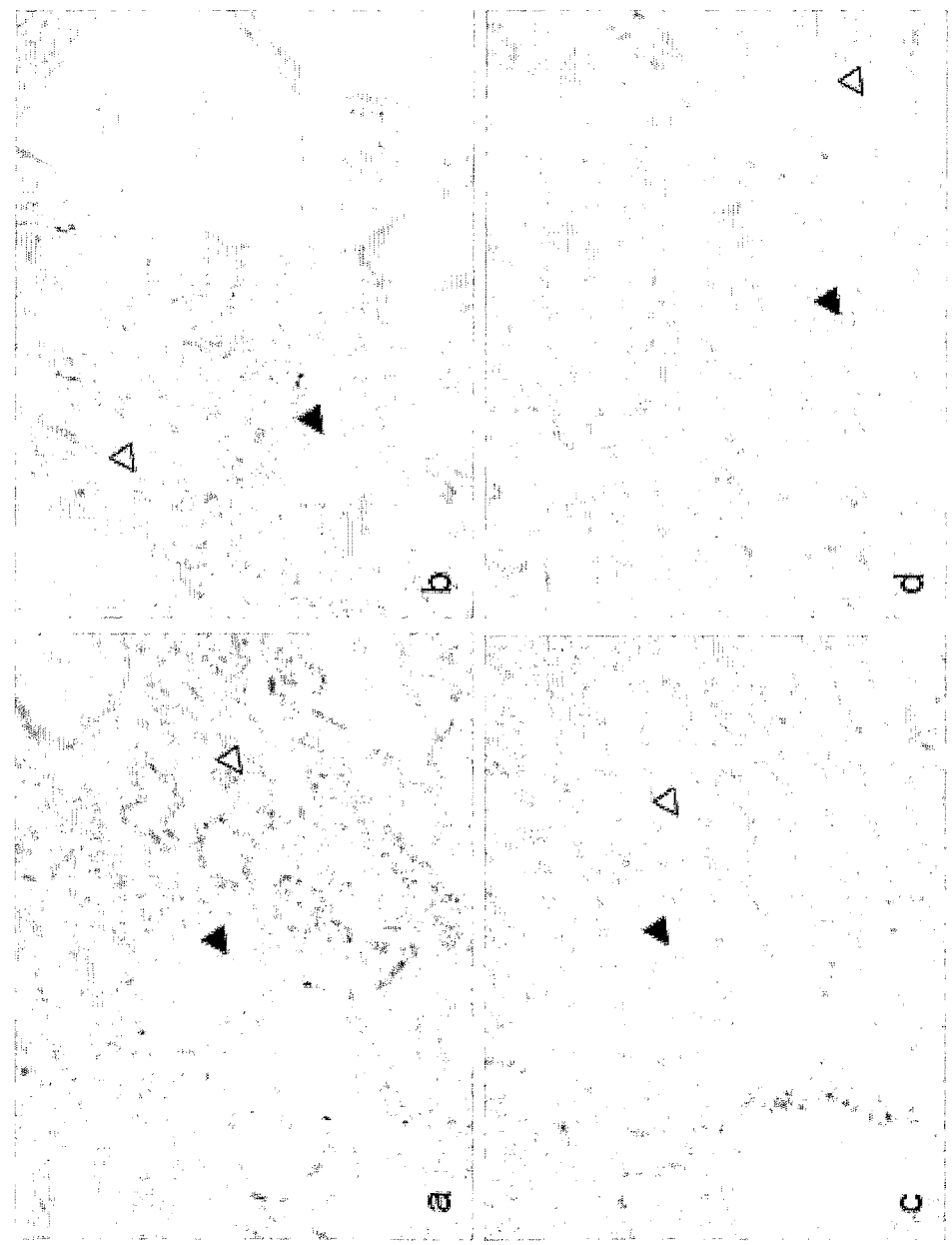
FIG. 4: Sections through TMA core biopsies of (a) normal prostate tissue, (b) benign hypertrophy of the prostate, and (c and d) malignant prostate tumour. EN-2 staining (brown) is present in the stromal cells (white filled arrow) and in the glands with strongest staining apparent at the luminal border (filled arrow heads). The nuclei are stained blue. Magnification: (a-c) ×60, (d) ×100.

To further examine the extent to which EN-2 is present in tissue from normal prostate, benign hypertrophy and malignant tumours, we stained a tissue microarray (TMA) containing representative sections from each with an anti-EN-2 antibody. This confirmed that EN-2 is expressed strongly in malignant glands, especially in the luminal borders (FIG. 4), although there is some staining in glands from normal and hypertrophic tissue. All tissues also showed EN-2 staining in the stromal cells (FIG. 4). In order to quantify staining in the glands each tissue was scored from 0 to 3 where 0 represents no staining and 3 the strongest staining. On this basis glands from normal tissue (FIG. 4a) scored a mean value of 0.5 (n=10, sd=0.52), from benign hyperplasia (FIG. 4b) 0.67 (n=6, sd=0.51), and from malignant tumours (FIG. 4c&d) 2.3 (n=6, sd=0.52).

These data clearly show that EN-2 is expressed in these prostate cancer cells.

EXAMPLE 4

Figure 5:
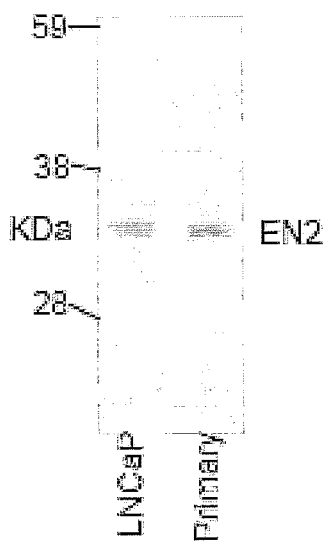
FIG. 5: Western blot detection of EN-2 protein in culture medium.

The medium surrounding LNCaP and primary prostate tumour cells was examined to establish whether EN-2 can be secreted from these cells. Medium, used to culture both cell types for two hours, was desalted and concentrated. Proteins contained within this concentrate were then resolved on an acrylamide gel. Western blotting revealed the presence of EN-2-specific bands in the medium surrounding both types of cells (FIG. 5), and quantification using standard amounts of in vitro-transcribed EN-2 protein indicated that the amount of EN-2 in the medium used to culture LNCaP cells was 3 ng/ml, whilst primary tumour cells produced 1.75 ng/ml in 48 hours.

EXAMPLE 5

Figure 6:
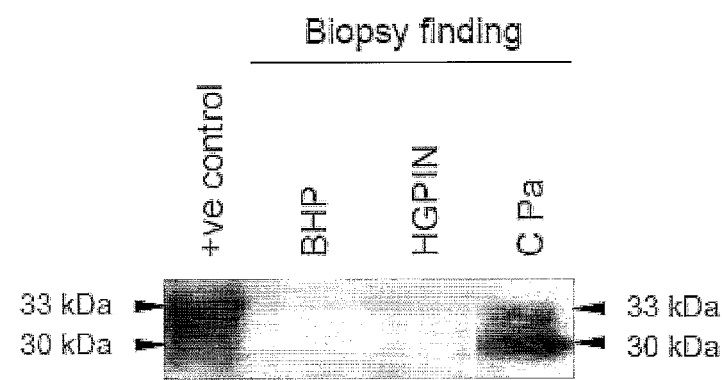
FIG. 6: EN-2 protein in urine. Urine was collected from individuals being examined for symptoms consistent with prostate cancer and screened for the presence of EN-2 protein. The presence of absence of cancer was tested for by biopsy. The predicted MW of EN-2 is 30 kDa but a second band of 33 kDa is also detected in the positive control (mouse cerebellum extract). The 30 kDa band is exclusively present in the urine of 50% of patients that had prostate cancer cells in their biopsy (C Pa), it was not present in patients with negative biopsies or with benign hypertrophy of the prostate (BHP) or high grade prostatic intraepithelial neoplasia (HGPIN).

Urine samples were obtained from 17 individuals, who had recently undergone prostatic biopsy and massage. Of these individuals, 10 were found to have cancer upon biopsy. Of the others, two had high grade prostatic intraepithelial neoplasia (HGPIN), three showed signs of benign hypertrophy and two had no cancerous cells in the biopsy section. Five of the patients diagnosed with cancer had large amounts of EN-2 in their urine, while none of the urine samples of the individuals not diagnosed with cancer contained a significant amount of EN-2 protein (FIG. 6).

EXAMPLE 6
HOXB5

The detection of HOXB5 in these samples was done exactly as for HOXC4 and HOXB6 except that the primary antibody was rabbit-anti human HOXB5 (from Abeam, cat no. ab26079). The relative values for HOXB5 protein were assessed by densitometry of the X-ray film (using the bands located at its predicted molecular weight). These values are the optical density of the band relative to that of the local background.

TABLE 3

| | Mean values | sd | sem | % increase |
|---|---|---|---|---|
| AMC | 0.006597 | 0.005948 | 0.003438 | 0 |
| Early ca | 0.244012 | 0.055004 | 0.031794 | 3598.808 |
| Late ca | 0.471597 | 0.154221 | 0.089145 | 7048.621 |

Figure 7:
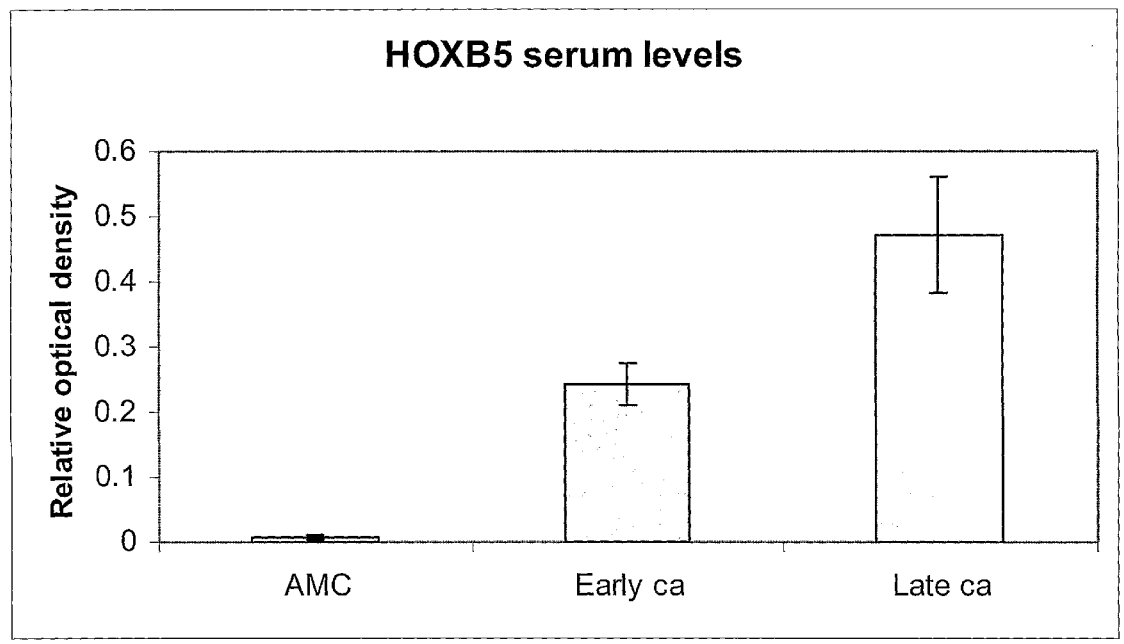
FIG. 7: Detection of HOXB5 in three patients with early stage prostate cancer where tumours are small and confined to the prostate, three patients with late stage prostate cancer and from three age-matched controls.

These data are represented graphically in FIG. 7.

EXAMPLE 7

Urine samples were obtained from 17 individuals, who were suspected to have prostate cancer and who were subsequently diagnosed with the disease. The protein levels of EN2 in the urine samples was assessed as described above. The urine samples of 8 (47%) of these individuals showed elevated levels of EN2. In contrast, in urine samples obtained from 15 patients who were suspected to have prostate cancer, but where the cancer was not confirmed subsequently, none (0%) had elevated levels of EN2. It is noteworthy that 3 of the patients diagnosed with prostate cancer, who showed elevated levels of EN2 in their urine samples, did not have elevated levels of PSA. This illustrates that the methods of the invention are effective at detecting cancer where conventional detection methods have failed.

EXAMPLE 8

Detection of Expression of HOX Genes in Normal and Tumour Tissue

RNA Extraction: Tumour and normal adjacent tissue RNA was purchased from Ambion, USA. RNA from cell cultures was extracted using the RNeasy Mini Kit (Qiagen, UK).

cDNA Synthesis: RNA was first denatured by heating to 65° C. for five minutes. 1-5 mg of RNA was incubated in a volume of 50 ml at 37° C. for one hour with final concentrations of 10 mM DTT, 1 mM dNTPmix, as well as 100 mg/ml polyT primers, 200 units of reverse transcriptase (Invitrogen, USA) and 40 units of RNASEout (Invitrogen, USA). The cDNA synthesis reaction was terminated by placing tubes at 65° C. for five minutes.

Real-Time PCR: Semi-quantitative RT-PCR was performed using the Stratagene MX4000 Real Time PCR machine. The Stratagene MX4000 measures PCR product accumulation during the exponential phase of the reaction, prior to the amplification becoming vulnerable to limited reagents and cycling variability. Fluorescence increases in accordance with increasing levels of PCR product. The relative amount of each transcript was determined as a ratio with the amount of Beta-actin transcript in each sample.

The primers used are listed in table 4 below.

| Gene | Forward primer | Reverse primer |
| --- | --- | --- |
| HOXA1 | CTGGCCCTGGCTACGTATAA (SEQ ID NO: 7) | TCCAACTTTCCCTGTTTTGG (SEQ ID NO: 8) |
| HOXA2 | TTCAGCAAAATGCCCTCTCT (SEQ ID NO: 9) | TAGGCCAGCTCCACAGTTCT (SEQ ID NO: 10) |
| HOXA3 | ACCTGTGATAGTGGGCTTGG (SEQ ID NO: 11) | ATACAGCCATTCCAGCAACC (SEQ ID NO: 12) |
| HOXA4 | CCCTGGATGAAGAAGATCCA (SEQ ID NO: 13) | AATTGGAGGATCGCATCTTG (SEQ ID NO: 14) |
| HOXA5 | CCGGAGAATGAAGTGGAAAA (SEQ ID NO: 15) | ACGAGAACAGGGCTTCTTCA (SEQ ID NO: 16) |
| HOXA6 | AAAGCACTCCATGACGAAGG (SEQ ID NO: 17) | TCCTTCTCCAGCTCCAGTGT (SEQ ID NO: 18) |
| HOXA7 | TGGTGTAAATCTGGGGGTGT (SEQ ID NO: 19) | TCTGATAAAGGGGGCTGTTG (SEQ ID NO: 20) |
| HOXA9 | AATAACCCAGCAGCCAACTG (SEQ ID NO: 21) | ATTTTCATCCTGCGGTTCTG (SEQ ID NO: 22) |
| HOXA10 | ACACTGGAGCTGGAGAAGGA (SEQ ID NO: 23) | GATCCGGTTTTCTCGATTCA (SEQ ID NO: 24) |
| HOXA11 | CGCTGCCCCTATACCAAGTA (SEQ ID NO: 25) | GTCAAGGGCAAAATCTGCAT (SEQ ID NO: 26) |
| HOXA13 | GGATATCAGCCACGACGAAT (SEQ ID NO: 27) | ATTATCTGGGCAAAGCAACG (SEQ ID NO: 28) |
| HOXD1 | TTCAGCACCAAGCAACTGAC (SEQ ID NO: 29) | TAGTGGGGGTTGTTCCAGAG (SEQ ID NO: 30) |
| HOXD3 | CAGCCTCCTGGTCTGAACTC (SEQ ID NO: 31) | ATCCAGGGGAAGATCTGCTT (SEQ ID NO: 32) |
| HOXD4 | TCAAATGTGCCATAGCAAGC (SEQ ID NO: 33) | TCCATAGGGCCCTCCTACTT (SEQ ID NO: 34) |
| HOXD8 | TCAAATGTTTCCGTGGATGA (SEQ ID NO: 35) | GCTCTTGGGCTTCCTTTTTC (SEQ ID NO: 36) |
| HOXD9 | TCCCCCATGTTTCTGAAAAG (SEQ ID NO: 37) | GGGCTCCTCTAAGCCTCACT (SEQ ID NO: 38) |
| HOXD10 | GCTCCTTCACCACCAACATT (SEQ ID NO: 39) | AAATATCCAGGGACGGGAAC (SEQ ID NO: 40) |
| HOXD11 | GGGGCTACGCTCCCTACTAC (SEQ ID NO: 41) | GCTGCCTCGTAGAACTGGTC (SEQ ID NO: 42) |
| HOXD12 | CGCTTCCCCCTATCTCCTAC (SEQ ID NO: 43) | CTTCGGGCGCATAGAACTTA (SEQ ID NO: 44) |
| HOXD13 | GGGGATGTGGCTCTAAATCA (SEQ ID NO: 45) | AACCTGGACCACATCAGGAG (SEQ ID NO: 46) |

Figure 8:
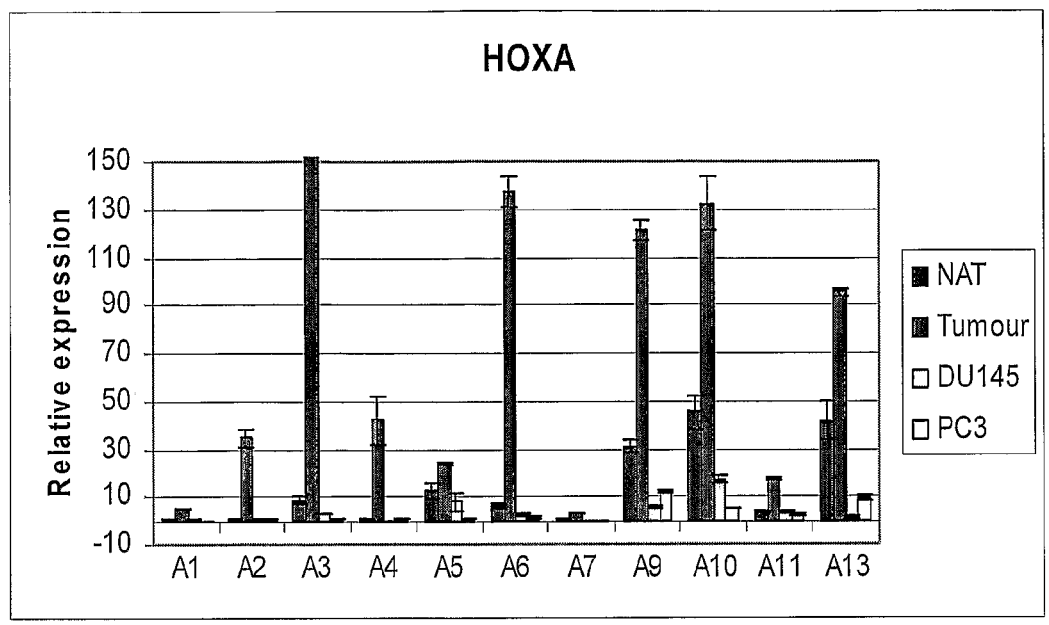
FIG. 8: Expression levels of various HOXA and HOXD genes in tumour tissue compared to normal adjacent tissue. DU145 and PC3 are cell lines derived from prostate tumours.
Figure 8:
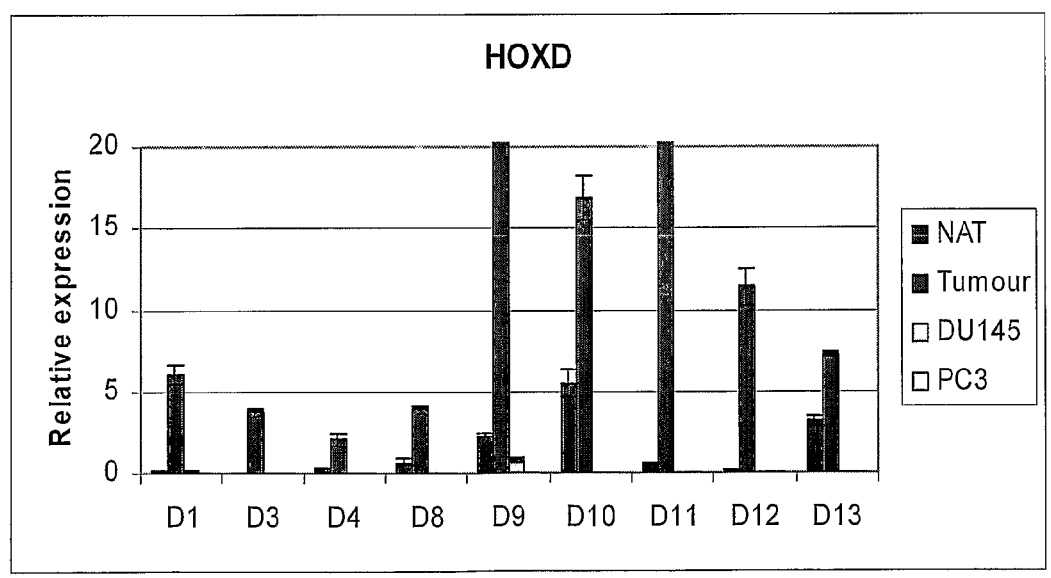

The results are shown in FIG. 8. Using this method, HOXA3 and HOXD9 were identified as potential biomarkers for prostate cancer, as these genes are clearly overexpressed in tumour tissue samples.

(HOXA3 polypeptide)
Sequence ID NO. 5
MQKATYYDSSAIYGGYPYQAANGFAYNANQQPYPASAALGADGE
YHRPACSLQSPSSAGGHPKAHELSEACLRTLSAPPSQPPSLGEPPLHPPP
PQAAPPAPQPPQPAPQPPAPTPAAPPPPSSASPPQNASNNPTPANAAKSP
LLNSPTVAKQIFPWMKESRQNTKQKTSSSSSGESCAGDKSPPGQASSKRA
RTAYTSAQLVELEKEFHFNRYLCRPRRVEMANLLNLTERQIKIWFQNRRM
KYKKDQKGKGMLTSSGGQSPSRSPVPPGAGGYLNSMHSLVNSVPYEPQSP
PPFSKPPQGTYGLPPASYPASLPSCAPPPPPQKRYTAAGAGAGGTPDYDP
HAHGLQGNGSYGTPHIQGSPVFVGGSYVEPMSNSGPALFGLTHLPHAASG
AMDYGGAGPLGSGHHHGPGPGEPHPTYTDLTGHHPSQGRIQEAPKLTHL (HOXD9 polypeptide)
Sequence ID NO. 6
MSSSGTLSNYYVDSLIGHEGDEVFAARFGPPGPGAQGRPAGVAD
GPAATAAEFASCSFAPRSAVFSASWSAVPSQPPAAAAMSGLYHPYVPPPP
LAASASEPGRYVRSWMEPLPGFPGGAGGGGGGGGGPGRGPSPGPSGPAN
GRHYGIKPETRAAPAPATAASTTSSSSTSLSSSSKRTECSVARESQGSSG
PEFSCNSFLQEKAAAATGGTGPGAGIGAATGTGGSSEPSACSDHPIPGCS
LKEEEKQHSQPQQQQLDPNNPAANWIHARSTRKKRCPYTKYQTLELEKEF
LFNMYLTRDRRYEVARILNLTERQVKIWFQNRRMKMKKMSKEKCPKGD

REFERENCES

Chatelin, L., Volovitch, M., Joliot, A. H., Perez, F. and Prochiantz, A. (1996) Transcription factor hoxa-5 is taken up by cells in culture and conveyed to their nuclei. Mech. Dev. 55, 111-117.

Cosgaya, J. M., Aranda, A., Cruces, J. and Martin-Blanco, E. (1998) Neuronal differentiation of PC12 cells induced by engrailed homeodomain is DNA-binding specific and independent of MAP kinases. J. Cell Sci. 111 (Pt 16), 2377-2384.

Derossi, D., Calvet, S., Trembleau, A., Brunissen, A., Chassaing, G. and Prochiantz, A. (1996) Cell internalization of the third helix of the Antennapedia homeodomain is receptor-independent. J. Biol. Chem. 271, 18188-18193.

Garcia-Bellido, A. and Santamaria, P. (1972) Developmental analysis of the wing disc in the mutant Engrailed of Drosophila melanogaster. Genetics 72, 87-104.

Joliot, A., Maizel, A., Rosenberg, D., Trembleau, A., Dupas, S., Volovitch, M. and Prochiantz, A. (1998) Identification of a signal sequence necessary for the unconventional secretion of Engrailed homeoprotein. Curr. Biol. 8, 856-863.

Kuefer R, Hofer M D, Zorn C S, Engel O, Volkmer B G, Juarez-Brito M A, Eggel M, Gschwend J E, Rubin M A, Day M L. Assessment of a fragment of e-cadherin as a serum biomarker with predictive value for prostate cancer. Br J Cancer. Jun. 6, 2005; 92(11):2018-23

Maizel, A., Bensaude, O., Prochiantz, A. and Joliot, A. (1999) A short region of its homeodomain is necessary for engrailed nuclear export and secretion. Development 126, 3183-3190.

Martin, N. L., Saba-El-Leil, M. K., Sadekova, S., Meloche, S. and Sauvageau, G. (2005) EN-2 is a candidate oncogene in human breast cancer. Oncogene 24, 6890-6901.

Miller G J, Miller H L, van Bokhoven A, Lambert J R, Werahera P N, Schirripa O, Lucia M S, Nordeen S K. Aberrant HOXC expression accompanies the malignant phenotype in human prostate. Cancer Res. Sep. 15, 2003; 63(18): 5879-88

Morgan R. Hox genes: a continuation of embryonic patterning? Trends Genet. 2006 February; 22(2):67-9.

Morgan R. Engrailed: complexity and economy of a multifunctional transcription factor. FEBS Lett. May 15, 2006; 580(11):2531-3

Petricoin E F, Ardekani A M, Hitt B A, Levine P J, Fusaro V A, Steinberg S M, Mills G B, Simone C, Fishman D A, Kohn E C, Liotta L A. Use of proteomic patterns in serum to identify ovarian cancer. Lancet. Feb. 16, 2002; 359(9306):572-7

The invention claimed is:

1. A method of diagnosing or monitoring the progression of prostate cancer in a subject, comprising detecting and/or quantifying at least one homeodomain containing transcription factor, or fragment thereof, in a urine sample from said subject;

comparing the level of the at least one homeodomain containing transcription factor, or fragment thereof, present in the urine sample with the level of the at least one homeodomain containing transcription factor, or fragment thereof, in one or more control samples; and determining that the subject is afflicted with prostate cancer or that the subject's prostate cancer has progressed if the level of the at least one homeodomain containing transcription factor, or fragment thereof, in the urine sample from said subject is increased relative to the level in the control sample;

wherein the at least one homeodomain containing transcription factor is an EN-2 peptide comprising SEQ ID NO:4; and wherein the fragment comprises at least ten consecutive amino acids from said SEQ ID NO:4, thereby diagnosing or monitoring the progression of prostate cancer in said subject.

2. The method according to claim 1, wherein at least two detection and/or quantification steps are provided, spaced apart temporally.

3. The method according to claim 2, wherein the at least two steps are spaced apart to determine whether the levels of the EN-2 peptide, or fragment thereof, have changed, thus indicating whether there has been a change in the progression of the cancer, enabling comparisons to be made between a level of the EN-2 peptide in samples taken on two or more occasions, wherein an increase in the level of the EN-2 peptide, or fragment thereof, over time is indicative of the onset or progression of the cancer, wherein a decrease in the level of the EN-2 peptide, or fragment thereof, may indicate amelioration and/or remission of the cancer.

4. A method of diagnosing prostate cancer a subject, comprising detecting and/or quantifying at least one homeodomain containing transcription factor, or fragment thereof, in a urine sample from said subject;

comparing the level of the at least one homeodomain containing transcription factor, or fragment thereof, present in the urine sample with the level of the at least one homeodomain containing transcription factor, or fragment thereof, present in a control sample from a normal, cancer-free, subject, and determining that the subject is afflicted with prostate cancer if the level of the at least one homeodomain containing transcription factor, or fragment thereof, in the urine sample from said subject is increased relative to the level in the control sample, wherein the homeodomain containing transcription factor is an EN-2 peptide comprising SEQ ID NO:4, wherein the fragment comprises at least ten consecutive amino acids from said SEQ ID NO:4, thereby diagnosing prostate cancer in said subject.

5. The method according to claim 4, wherein the statistical significance of the increase is determined by using a "t-test" providing confidence intervals of at least 80%, at least 85%, at least 90%, at least 95%, at least 99%, at least 99.5%, at least 99.95%, or at least 99.99%.

6. The method according to claim 4, wherein the increase between the control sample and the urine sample is about 110-200%, or about 125%, and is indicative of early stage prostate cancer.

7. The method according to claim 4, wherein the increase between the control sample and the urine sample is about 550-620%, or about 560-600%, or about 570-590%, or about 580%, and is indicative of late stage prostate cancer.

8. The method according to claim 4, wherein the increase between the control sample and the urine sample is about 100%-300%, or about 200% and is indicative of progression of the cancer from early to late stage disease.

9. A method of monitoring the efficacy of a treatment for prostate cancer, the method comprising
   detecting and/or quantifying at least one homeodomain containing transcription factor, or a fragment thereof, present in two temporally separated urine samples from a subject receiving said treatment;
   comparing the levels of the at least one homeodomain containing transcription factor, or a fragment thereof, in the two urine samples; and
   determining that the treatment is effective if a temporal decrease in the level of the at least one homeodomain containing transcription factor, or a fragment thereof, is found; or
   determining that the treatment is not effective if a temporal increase in the level of the at least one homeodomain containing transcription factor, or a fragment thereof, is found;
   wherein the at least one homeodomain containing transcription factor is an EN-2 peptide comprising SEQ ID NO: 4,
   wherein the fragment comprises at least ten consecutive amino acids from said SEQ ID NO:4, thereby monitoring the efficacy of a treatment for prostate cancer.

10. The method according to claim 1, 4 or 9, wherein detection and/or quantification of the at least one homeodomain containing transcription factor, or fragment thereof, is achieved by a method selected from MALDI-TOF, SELDI, via interaction with a ligand or ligands, 1-D or 2-D gel-based analysis systems, Liquid Chromatography combined with Mass spectrometry techniques, thin-layer chromatography, and NMR spectroscopy.

11. The method according to claim 1, 4, or 9, wherein detection and/or quantification of the at least one homeodomain containing transcription factor, or fragment thereof, is achieved by a method selected from sandwich immunoassays, enzyme linked immunosorbent assays (ELISAs), radio-immunoassays (RAI), enzyme immunoassays (EIA), Western Blotting, immunoprecipitation, and particle-based immunoassays including using gold, silver, or latex particles, magnetic particles, or quantum dots.

12. The method according to claim 1, wherein the urine sample is free of whole or intact cells.

13. The method of according to claim 1, wherein the urine sample is from a subject that has previously been diagnosed as negative for cancer using an assay which detects PSA.

14. The method according to claim 11, wherein detection and/or quantification of the at least one homeodomain containing transcription factor, or a fragment thereof, is performed on microtitre plate, strip format, array or on a chip.

15. The method of claim 1, 4 or 9, wherein the at least one homeodomain containing transcription factor, or fragment thereof, is detected directly or indirectly via interaction with a ligand.

16. The method of claim 15, wherein the ligand is selected from the group consisting of an anti-EN-2 antibody or a binding fragment thereof, an aptamer, and an oligonucleotide.

17. The method of claim 1 or 9, wherein the control is taken from a normal subject.

18. The method of claim 1 or 9, wherein the urine sample and control are both taken from the same subject, and wherein the control is taken prior to the incidence of disease.

* * * * *

SEQUENCE LISTING

```
<160> NUMBER OF SEQ ID NOS: 46

<210> SEQ ID NO 1
<211> LENGTH: 264
<212> TYPE: PRT
<213> ORGANISM: Homo sapiens

<400> SEQUENCE: 1

Met Ile Met Ser Ser Tyr Leu Met Asp Ser Asn Tyr Ile Asp Pro Lys
1               5                   10                  15

Phe Pro Pro Cys Glu Glu Tyr Ser Gln Asn Ser Tyr Ile Pro Glu His
            20                  25                  30

Ser Pro Glu Tyr Tyr Gly Arg Thr Arg Glu Ser Gly Phe Gln His His
        35                  40                  45

His Gln Glu Leu Tyr Pro Pro Pro Pro Arg Pro Ser Tyr Pro Glu
    50                  55                  60

Arg Gln Tyr Ser Cys Thr Ser Leu Gln Gly Pro Gly Asn Ser Arg Gly
65                  70                  75                  80

His Gly Pro Ala Gln Ala Gly His His Pro Glu Lys Ser Gln Ser
                85                  90                  95

Leu Cys Glu Pro Ala Pro Leu Ser Gly Ala Ser Ala Ser Pro Ser Pro
            100                 105                 110

Ala Pro Pro Ala Cys Ser Gln Pro Ala Pro Asp His Pro Ser Ser Ala
            115                 120                 125

Ala Ser Lys Gln Pro Ile Val Tyr Pro Trp Met Lys Lys Ile His Val
        130                 135                 140

Ser Thr Val Asn Pro Asn Tyr Asn Gly Gly Glu Pro Lys Arg Ser Arg
145                 150                 155                 160

Ala Ala Tyr Thr Arg Gln Gln Val Leu Glu Leu Glu Lys Glu Phe His
                165                 170                 175

Tyr Asn Arg Tyr Leu Thr Arg Arg Arg Ile Glu Ile Ala His Ser
            180                 185                 190

Leu Cys Leu Ser Glu Arg Gln Ile Lys Ile Trp Phe Gln Asn Arg Arg
        195                 200                 205

Met Lys Trp Lys Lys Asp His Arg Leu Pro Asn Thr Lys Val Arg Ser
```

```
                     210                 215                 220

Ala Pro Pro Ala Gly Ala Pro Ser Thr Leu Ser Ala Ala Thr Pro
225                 230                 235                 240

Gly Thr Ser Glu Asp His Ser Gln Ser Ala Thr Pro Pro Gln Gln
                    245                 250                 255

Arg Ala Glu Asp Ile Thr Arg Leu
            260

<210> SEQ ID NO 2
<211> LENGTH: 224
<212> TYPE: PRT
<213> ORGANISM: Homo sapiens

<400> SEQUENCE: 2

Met Ser Ser Tyr Phe Val Asn Ser Thr Phe Pro Val Thr Leu Ala Ser
1               5                   10                  15

Gly Gln Glu Ser Phe Leu Gly Gln Leu Pro Leu Tyr Ser Ser Gly Tyr
                20                  25                  30

Ala Asp Pro Leu Arg His Tyr Pro Ala Pro Tyr Gly Pro Gly Pro Gly
            35                  40                  45

Gln Asp Lys Gly Phe Ala Thr Ser Ser Tyr Tyr Pro Pro Ala Gly Gly
        50                  55                  60

Gly Tyr Gly Arg Ala Ala Pro Cys Asp Tyr Gly Pro Ala Pro Ala Phe
65                  70                  75                  80

Tyr Arg Glu Lys Glu Ser Ala Cys Ala Leu Ser Gly Ala Asp Glu Gln
                85                  90                  95

Pro Pro Phe His Pro Glu Pro Arg Lys Ser Asp Cys Ala Gln Asp Lys
            100                 105                 110

Ser Val Phe Gly Glu Thr Glu Glu Gln Lys Cys Ser Thr Pro Val Tyr
        115                 120                 125

Pro Trp Met Gln Arg Met Asn Ser Cys Asn Ser Ser Phe Gly Pro
130                 135                 140

Ser Gly Arg Arg Gly Arg Gln Thr Tyr Thr Arg Tyr Gln Thr Leu Glu
145                 150                 155                 160

Leu Glu Lys Glu Phe His Tyr Asn Arg Tyr Leu Thr Arg Arg Arg
                165                 170                 175

Ile Glu Ile Ala His Ala Leu Cys Leu Thr Glu Arg Gln Ile Lys Ile
            180                 185                 190

Trp Phe Gln Asn Arg Arg Met Lys Trp Lys Lys Glu Ser Lys Leu Leu
        195                 200                 205

Ser Ala Ser Gln Leu Ser Ala Glu Glu Glu Glu Lys Gln Ala Glu
    210                 215                 220

<210> SEQ ID NO 3
<211> LENGTH: 269
<212> TYPE: PRT
<213> ORGANISM: Homo sapiens

<400> SEQUENCE: 3

Met Ser Ser Tyr Phe Val Asn Ser Phe Ser Gly Arg Tyr Pro Asn Gly
1               5                   10                  15

Pro Asp Tyr Gln Leu Leu Asn Tyr Gly Ser Gly Ser Ser Leu Ser Gly
                20                  25                  30

Ser Tyr Arg Asp Pro Ala Ala Met His Thr Gly Ser Tyr Gly Tyr Asn
            35                  40                  45

Tyr Asn Gly Met Asp Leu Ser Val Asn Arg Ser Ser Ala Ser Ser Ser
        50                  55                  60
```

```
His Phe Gly Ala Val Gly Glu Ser Ser Arg Ala Phe Pro Ala Pro Ala
 65                  70                  75                  80

Gln Glu Pro Arg Phe Arg Gln Ala Ala Ser Cys Ser Leu Ser Ser
                 85                  90                  95

Pro Glu Ser Leu Pro Cys Thr Asn Gly Asp Ser His Gly Ala Lys Pro
                100                 105                 110

Ser Ala Ser Ser Pro Ser Asp Gln Ala Thr Ser Ala Ser Ser Ser Ala
            115                 120                 125

Asn Phe Thr Glu Ile Asp Glu Ala Ser Ala Ser Ser Glu Pro Glu Glu
        130                 135                 140

Ala Ala Ser Gln Leu Ser Ser Pro Ser Leu Ala Arg Ala Gln Pro Glu
145                 150                 155                 160

Pro Met Ala Thr Ser Thr Ala Ala Pro Glu Gly Gln Thr Pro Gln Ile
                165                 170                 175

Phe Pro Trp Met Arg Lys Leu His Ile Ser His Asp Met Thr Gly Pro
                180                 185                 190

Asp Gly Lys Arg Ala Arg Thr Ala Tyr Thr Arg Tyr Gln Thr Leu Glu
            195                 200                 205

Leu Glu Lys Glu Phe His Phe Asn Arg Tyr Leu Thr Arg Arg Arg Arg
        210                 215                 220

Ile Glu Ile Ala His Ala Leu Cys Leu Ser Glu Arg Gln Ile Lys Ile
225                 230                 235                 240

Trp Phe Gln Asn Arg Met Lys Trp Lys Lys Asp Asn Lys Leu Lys
                245                 250                 255

Ser Met Ser Leu Ala Thr Ala Gly Ser Ala Phe Gln Pro
                260                 265

<210> SEQ ID NO 4
<211> LENGTH: 333
<212> TYPE: PRT
<213> ORGANISM: Homo sapiens

<400> SEQUENCE: 4

Met Glu Glu Asn Asp Pro Lys Pro Gly Glu Ala Ala Ala Val Glu
 1                5                  10                  15

Gly Gln Arg Gln Pro Glu Ser Ser Pro Gly Gly Gly Ser Gly Gly Gly
                 20                  25                  30

Gly Gly Ser Ser Pro Gly Glu Ala Asp Thr Gly Arg Arg Arg Ala Leu
            35                  40                  45

Met Leu Pro Ala Val Leu Gln Ala Pro Gly Asn His Gln His Pro His
        50                  55                  60

Arg Ile Thr Asn Phe Phe Ile Asp Asn Ile Leu Arg Pro Glu Phe Gly
 65                  70                  75                  80

Arg Arg Lys Asp Ala Gly Thr Cys Cys Ala Gly Ala Gly Gly Gly Arg
                 85                  90                  95

Gly Gly Gly Ala Gly Gly Glu Gly Gly Ala Ser Gly Ala Glu Gly Gly
                100                 105                 110

Gly Gly Ala Gly Gly Ser Glu Gln Leu Leu Gly Ser Gly Ser Arg Glu
            115                 120                 125

Pro Arg Gln Asn Pro Pro Cys Ala Pro Ala Gly Gly Pro Leu Pro
        130                 135                 140

Ala Ala Gly Ser Asp Ser Pro Gly Asp Gly Glu Gly Ser Lys Thr
145                 150                 155                 160

Leu Ser Leu His Gly Gly Ala Lys Lys Gly Gly Asp Pro Gly Gly Pro
                165                 170                 175
```

```
Leu Asp Gly Ser Leu Lys Ala Arg Gly Leu Gly Gly Asp Leu Ser
            180                 185                 190

Val Ser Ser Asp Ser Asp Ser Ser Gln Ala Gly Ala Asn Leu Gly Ala
        195                 200                 205

Gln Pro Met Leu Trp Pro Ala Trp Val Tyr Cys Thr Arg Tyr Ser Asp
210                 215                 220

Arg Pro Ser Ser Gly Pro Arg Ser Arg Lys Pro Lys Lys Asn Pro
225                 230                 235                 240

Asn Lys Glu Asp Lys Arg Pro Arg Thr Ala Phe Thr Ala Glu Gln Leu
                245                 250                 255

Gln Arg Leu Lys Ala Glu Phe Gln Thr Asn Arg Tyr Leu Thr Glu Gln
            260                 265                 270

Arg Arg Gln Ser Leu Ala Gln Glu Leu Ser Leu Asn Glu Ser Gln Ile
        275                 280                 285

Lys Ile Trp Phe Gln Asn Lys Arg Ala Lys Ile Lys Lys Ala Thr Gly
290                 295                 300

Asn Lys Asn Thr Leu Ala Val His Leu Met Ala Gln Gly Leu Tyr Asn
305                 310                 315                 320

His Ser Thr Thr Ala Lys Glu Gly Lys Ser Asp Ser Glu
                325                 330

<210> SEQ ID NO 5
<211> LENGTH: 443
<212> TYPE: PRT
<213> ORGANISM: Homo sapiens

<400> SEQUENCE: 5

Met Gln Lys Ala Thr Tyr Tyr Asp Ser Ser Ala Ile Tyr Gly Gly Tyr
1               5                   10                  15

Pro Tyr Gln Ala Ala Asn Gly Phe Ala Tyr Asn Ala Asn Gln Gln Pro
            20                  25                  30

Tyr Pro Ala Ser Ala Ala Leu Gly Ala Asp Gly Glu Tyr His Arg Pro
        35                  40                  45

Ala Cys Ser Leu Gln Ser Pro Ser Ser Ala Gly Gly His Pro Lys Ala
    50                  55                  60

His Glu Leu Ser Glu Ala Cys Leu Arg Thr Leu Ser Ala Pro Pro Ser
65                  70                  75                  80

Gln Pro Pro Ser Leu Gly Glu Pro Pro Leu His Pro Pro Pro Gln
                85                  90                  95

Ala Ala Pro Pro Ala Pro Gln Pro Gln Pro Ala Pro Gln Pro Pro
            100                 105                 110

Ala Pro Thr Pro Ala Ala Pro Pro Pro Ser Ser Ala Ser Pro Pro
        115                 120                 125

Gln Asn Ala Ser Asn Asn Pro Thr Pro Ala Asn Ala Ala Lys Ser Pro
    130                 135                 140

Leu Leu Asn Ser Pro Thr Val Ala Lys Gln Ile Phe Pro Trp Met Lys
145                 150                 155                 160

Glu Ser Arg Gln Asn Thr Lys Gln Lys Thr Ser Ser Ser Ser Ser Gly
                165                 170                 175

Glu Ser Cys Ala Gly Asp Lys Ser Pro Pro Gly Gln Ala Ser Ser Lys
            180                 185                 190

Arg Ala Arg Thr Ala Tyr Thr Ser Ala Gln Leu Val Glu Leu Glu Lys
        195                 200                 205

Glu Phe His Phe Asn Arg Tyr Leu Cys Arg Pro Arg Arg Val Glu Met
    210                 215                 220
```

```
Ala Asn Leu Leu Asn Leu Thr Glu Arg Gln Ile Lys Ile Trp Phe Gln
225                 230                 235                 240

Asn Arg Arg Met Lys Tyr Lys Lys Asp Gln Lys Gly Lys Gly Met Leu
            245                 250                 255

Thr Ser Ser Gly Gly Gln Ser Pro Ser Arg Ser Pro Val Pro Pro Gly
                260                 265                 270

Ala Gly Gly Tyr Leu Asn Ser Met His Ser Leu Val Asn Ser Val Pro
            275                 280                 285

Tyr Glu Pro Gln Ser Pro Pro Phe Ser Lys Pro Gln Gly Thr
290                 295                 300

Tyr Gly Leu Pro Pro Ala Ser Tyr Pro Ala Ser Leu Pro Ser Cys Ala
305                 310                 315                 320

Pro Pro Pro Pro Gln Lys Arg Tyr Thr Ala Ala Gly Ala Gly Ala
                325                 330                 335

Gly Gly Thr Pro Asp Tyr Asp Pro His Ala His Gly Leu Gln Gly Asn
            340                 345                 350

Gly Ser Tyr Gly Thr Pro His Ile Gln Gly Ser Pro Val Phe Val Gly
            355                 360                 365

Gly Ser Tyr Val Glu Pro Met Ser Asn Ser Gly Pro Ala Leu Phe Gly
            370                 375                 380

Leu Thr His Leu Pro His Ala Ala Ser Gly Ala Met Asp Tyr Gly Gly
385                 390                 395                 400

Ala Gly Pro Leu Gly Ser Gly His His Gly Pro Gly Pro Gly Glu
                405                 410                 415

Pro His Pro Thr Tyr Thr Asp Leu Thr Gly His His Pro Ser Gln Gly
                420                 425                 430

Arg Ile Gln Glu Ala Pro Lys Leu Thr His Leu
            435                 440

<210> SEQ ID NO 6
<211> LENGTH: 342
<212> TYPE: PRT
<213> ORGANISM: Homo sapiens

<400> SEQUENCE: 6

Met Ser Ser Ser Gly Thr Leu Ser Asn Tyr Tyr Val Asp Ser Leu Ile
1               5                   10                  15

Gly His Glu Gly Asp Glu Val Phe Ala Ala Arg Phe Gly Pro Pro Gly
            20                  25                  30

Pro Gly Ala Gln Gly Arg Pro Ala Gly Val Ala Asp Gly Pro Ala Ala
            35                  40                  45

Thr Ala Ala Glu Phe Ala Ser Cys Ser Phe Ala Pro Arg Ser Ala Val
50                  55                  60

Phe Ser Ala Ser Trp Ser Ala Val Pro Ser Gln Pro Pro Ala Ala Ala
65                  70                  75                  80

Ala Met Ser Gly Leu Tyr His Pro Tyr Val Pro Pro Pro Leu Ala
                85                  90                  95

Ala Ser Ala Ser Glu Pro Gly Arg Tyr Val Arg Ser Trp Met Glu Pro
            100                 105                 110

Leu Pro Gly Phe Pro Gly Gly Ala Gly Gly Gly Gly Gly Gly Gly
            115                 120                 125

Gly Gly Pro Gly Arg Gly Pro Ser Pro Gly Ser Gly Pro Ala Asn
        130                 135                 140

Gly Arg His Tyr Gly Ile Lys Pro Glu Thr Arg Ala Ala Pro Ala Pro
145                 150                 155                 160
```

```
Ala Thr Ala Ala Ser Thr Thr Ser Ser Ser Thr Ser Leu Ser Ser
            165                 170                 175

Ser Ser Lys Arg Thr Glu Cys Ser Val Ala Arg Glu Ser Gln Gly Ser
        180                 185                 190

Ser Gly Pro Glu Phe Ser Cys Asn Ser Phe Leu Gln Glu Lys Ala Ala
            195                 200                 205

Ala Ala Thr Gly Gly Thr Gly Pro Gly Ala Gly Ile Gly Ala Ala Thr
    210                 215                 220

Gly Thr Gly Gly Ser Ser Glu Pro Ser Ala Cys Ser Asp His Pro Ile
225                 230                 235                 240

Pro Gly Cys Ser Leu Lys Glu Glu Lys Gln His Ser Gln Pro Gln
                245                 250                 255

Gln Gln Gln Leu Asp Pro Asn Asn Pro Ala Ala Asn Trp Ile His Ala
            260                 265                 270

Arg Ser Thr Arg Lys Lys Arg Cys Pro Tyr Thr Lys Tyr Gln Thr Leu
        275                 280                 285

Glu Leu Glu Lys Glu Phe Leu Phe Asn Met Tyr Leu Thr Arg Asp Arg
    290                 295                 300

Arg Tyr Glu Val Ala Arg Ile Leu Asn Leu Thr Glu Arg Gln Val Lys
305                 310                 315                 320

Ile Trp Phe Gln Asn Arg Arg Met Lys Met Lys Met Ser Lys Glu
                325                 330                 335

Lys Cys Pro Lys Gly Asp
            340

<210> SEQ ID NO 7
<211> LENGTH: 20
<212> TYPE: DNA
<213> ORGANISM: Artificial Sequence
<220> FEATURE:
<223> OTHER INFORMATION: Primer HOXA1 forwards

<400> SEQUENCE: 7
ctggccctgg ctacgtataa                                               20

<210> SEQ ID NO 8
<211> LENGTH: 20
<212> TYPE: DNA
<213> ORGANISM: Artificial Sequence
<220> FEATURE:
<223> OTHER INFORMATION: Primer HOXA1 reverse

<400> SEQUENCE: 8
tccaactttc cctgttttgg                                               20

<210> SEQ ID NO 9
<211> LENGTH: 20
<212> TYPE: DNA
<213> ORGANISM: Artificial Sequence
<220> FEATURE:
<223> OTHER INFORMATION: Primer HOXA2 forwards

<400> SEQUENCE: 9
ttcagcaaaa tgccctctct                                               20

<210> SEQ ID NO 10
<211> LENGTH: 20
<212> TYPE: DNA
<213> ORGANISM: Artificial Sequence
<220> FEATURE:
<223> OTHER INFORMATION: Primer HOXA2 reverse
```

```
<400> SEQUENCE: 10
taggccagct ccacagttct                                              20

<210> SEQ ID NO 11
<211> LENGTH: 20
<212> TYPE: DNA
<213> ORGANISM: Artificial Sequence
<220> FEATURE:
<223> OTHER INFORMATION: Primer HOXA3 forwards

<400> SEQUENCE: 11
acctgtgata gtgggcttgg                                              20

<210> SEQ ID NO 12
<211> LENGTH: 20
<212> TYPE: DNA
<213> ORGANISM: Artificial Sequence
<220> FEATURE:
<223> OTHER INFORMATION: Primer HOXA3 reverse

<400> SEQUENCE: 12
atacagccat tccagcaacc                                              20

<210> SEQ ID NO 13
<211> LENGTH: 20
<212> TYPE: DNA
<213> ORGANISM: Artificial Sequence
<220> FEATURE:
<223> OTHER INFORMATION: Primer HOXA4 forwards

<400> SEQUENCE: 13
ccctggatga agaagatcca                                              20

<210> SEQ ID NO 14
<211> LENGTH: 20
<212> TYPE: DNA
<213> ORGANISM: Artificial Sequence
<220> FEATURE:
<223> OTHER INFORMATION: Primer HOXA4 reverse

<400> SEQUENCE: 14
aattggagga tcgcatcttg                                              20

<210> SEQ ID NO 15
<211> LENGTH: 20
<212> TYPE: DNA
<213> ORGANISM: Artificial Sequence
<220> FEATURE:
<223> OTHER INFORMATION: Primer HOXA5 forwards

<400> SEQUENCE: 15
ccggagaatg aagtggaaaa                                              20

<210> SEQ ID NO 16
<211> LENGTH: 20
<212> TYPE: DNA
<213> ORGANISM: Artificial Sequence
<220> FEATURE:
<223> OTHER INFORMATION: Primer HOXA5 reverse

<400> SEQUENCE: 16
acgagaacag ggcttcttca                                              20

<210> SEQ ID NO 17
<211> LENGTH: 20
```

-continued

<210> SEQ ID NO 17
<211> LENGTH: 20
<212> TYPE: DNA
<213> ORGANISM: Artificial Sequence
<220> FEATURE:
<223> OTHER INFORMATION: Primer HOXA6 forwards

<400> SEQUENCE: 17
aaagcactcc atgacgaagg         20

<210> SEQ ID NO 18
<211> LENGTH: 20
<212> TYPE: DNA
<213> ORGANISM: Artificial Sequence
<220> FEATURE:
<223> OTHER INFORMATION: Primer HOXA6 reverse

<400> SEQUENCE: 18
tccttctcca gctccagtgt         20

<210> SEQ ID NO 19
<211> LENGTH: 20
<212> TYPE: DNA
<213> ORGANISM: Artificial Sequence
<220> FEATURE:
<223> OTHER INFORMATION: Primer HOXA7 forwards

<400> SEQUENCE: 19
tggtgtaaat ctgggggtgt         20

<210> SEQ ID NO 20
<211> LENGTH: 20
<212> TYPE: DNA
<213> ORGANISM: Artificial Sequence
<220> FEATURE:
<223> OTHER INFORMATION: Primer HOXA7 reverse

<400> SEQUENCE: 20
tctgataaag ggggctgttg         20

<210> SEQ ID NO 21
<211> LENGTH: 20
<212> TYPE: DNA
<213> ORGANISM: Artificial Sequence
<220> FEATURE:
<223> OTHER INFORMATION: Primer HOXA9 forwards

<400> SEQUENCE: 21
aataacccag cagccaactg         20

<210> SEQ ID NO 22
<211> LENGTH: 20
<212> TYPE: DNA
<213> ORGANISM: Artificial Sequence
<220> FEATURE:
<223> OTHER INFORMATION: Primer HOXA9 reverse

<400> SEQUENCE: 22
attttcatcc tgcggttctg         20

<210> SEQ ID NO 23
<211> LENGTH: 20
<212> TYPE: DNA
<213> ORGANISM: Artificial Sequence
<220> FEATURE:
<223> OTHER INFORMATION: Primer HOXA10 forwards

<400> SEQUENCE: 23
acactggagc tggagaagga         20

<210> SEQ ID NO 24
<211> LENGTH: 20
<212> TYPE: DNA
<213> ORGANISM: Artificial Sequence
<220> FEATURE:
<223> OTHER INFORMATION: Primer HOXA10 reverse

<400> SEQUENCE: 24
gatccggttt tctcgattca                                        20

<210> SEQ ID NO 25
<211> LENGTH: 20
<212> TYPE: DNA
<213> ORGANISM: Artificial Sequence
<220> FEATURE:
<223> OTHER INFORMATION: Primer HOXA11 forwards

<400> SEQUENCE: 25
cgctgcccct ataccaagta                                        20

<210> SEQ ID NO 26
<211> LENGTH: 20
<212> TYPE: DNA
<213> ORGANISM: Artificial Sequence
<220> FEATURE:
<223> OTHER INFORMATION: Primer HOXA11 reverse

<400> SEQUENCE: 26
gtcaagggca aaatctgcat                                        20

<210> SEQ ID NO 27
<211> LENGTH: 20
<212> TYPE: DNA
<213> ORGANISM: Artificial Sequence
<220> FEATURE:
<223> OTHER INFORMATION: Primer HOXA13 forwards

<400> SEQUENCE: 27
ggatatcagc cacgacgaat                                        20

<210> SEQ ID NO 28
<211> LENGTH: 20
<212> TYPE: DNA
<213> ORGANISM: Artificial Sequence
<220> FEATURE:
<223> OTHER INFORMATION: Primer HOXA13 reverse

<400> SEQUENCE: 28
attatctggg caaagcaacg                                        20

<210> SEQ ID NO 29
<211> LENGTH: 20
<212> TYPE: DNA
<213> ORGANISM: Artificial Sequence
<220> FEATURE:
<223> OTHER INFORMATION: Primer HOXD1 forwards

<400> SEQUENCE: 29
ttcagcacca agcaactgac                                        20

<210> SEQ ID NO 30
<211> LENGTH: 20
<212> TYPE: DNA
<213> ORGANISM: Artificial Sequence
<220> FEATURE:
<223> OTHER INFORMATION: Primer HOXD1 reverse

```
<400> SEQUENCE: 30
tagtgggggt tgttccagag                                               20

<210> SEQ ID NO 31
<211> LENGTH: 20
<212> TYPE: DNA
<213> ORGANISM: Artificial Sequence
<220> FEATURE:
<223> OTHER INFORMATION: Primer HOXD3 forwards

<400> SEQUENCE: 31
cagcctcctg gtctgaactc                                               20

<210> SEQ ID NO 32
<211> LENGTH: 20
<212> TYPE: DNA
<213> ORGANISM: Artificial Sequence
<220> FEATURE:
<223> OTHER INFORMATION: Primer HOXD3 reverse

<400> SEQUENCE: 32
atccagggga agatctgctt                                               20

<210> SEQ ID NO 33
<211> LENGTH: 20
<212> TYPE: DNA
<213> ORGANISM: Artificial Sequence
<220> FEATURE:
<223> OTHER INFORMATION: Primer HOXD4 forwards

<400> SEQUENCE: 33
tcaaatgtgc catagcaagc                                               20

<210> SEQ ID NO 34
<211> LENGTH: 20
<212> TYPE: DNA
<213> ORGANISM: Artificial Sequence
<220> FEATURE:
<223> OTHER INFORMATION: Primer HOXD4 reverse

<400> SEQUENCE: 34
tccatagggc cctcctactt                                               20

<210> SEQ ID NO 35
<211> LENGTH: 20
<212> TYPE: DNA
<213> ORGANISM: Artificial Sequence
<220> FEATURE:
<223> OTHER INFORMATION: Primer HOXD8 forwards

<400> SEQUENCE: 35
tcaaatgttt ccgtggatga                                               20

<210> SEQ ID NO 36
<211> LENGTH: 20
<212> TYPE: DNA
<213> ORGANISM: Artificial Sequence
<220> FEATURE:
<223> OTHER INFORMATION: Primer HOXD8 reverse

<400> SEQUENCE: 36
gctcttgggc ttcctttttc                                               20

<210> SEQ ID NO 37
<211> LENGTH: 20
```

<210> SEQ ID NO 37
<211> LENGTH: 20
<212> TYPE: DNA
<213> ORGANISM: Artificial Sequence
<220> FEATURE:
<223> OTHER INFORMATION: Primer HOXD9 forwards

<400> SEQUENCE: 37
tcccccatgt ttctgaaaag                                           20

<210> SEQ ID NO 38
<211> LENGTH: 20
<212> TYPE: DNA
<213> ORGANISM: Artificial Sequence
<220> FEATURE:
<223> OTHER INFORMATION: Primer HOXD9 reverse

<400> SEQUENCE: 38
gggctcctct aagcctcact                                           20

<210> SEQ ID NO 39
<211> LENGTH: 20
<212> TYPE: DNA
<213> ORGANISM: Artificial Sequence
<220> FEATURE:
<223> OTHER INFORMATION: Primer HOXD10 forwards

<400> SEQUENCE: 39
gctccttcac caccaacatt                                           20

<210> SEQ ID NO 40
<211> LENGTH: 20
<212> TYPE: DNA
<213> ORGANISM: Artificial Sequence
<220> FEATURE:
<223> OTHER INFORMATION: Primer HOXD10 reverse

<400> SEQUENCE: 40
aaatatccag ggacgggaac                                           20

<210> SEQ ID NO 41
<211> LENGTH: 20
<212> TYPE: DNA
<213> ORGANISM: Artificial Sequence
<220> FEATURE:
<223> OTHER INFORMATION: Primer HOXD11 forwards

<400> SEQUENCE: 41
ggggctacgc tccctactac                                           20

<210> SEQ ID NO 42
<211> LENGTH: 20
<212> TYPE: DNA
<213> ORGANISM: Artificial Sequence
<220> FEATURE:
<223> OTHER INFORMATION: Primer HOXD11 reverse

<400> SEQUENCE: 42
gctgcctcgt agaactggtc                                           20

<210> SEQ ID NO 43
<211> LENGTH: 20
<212> TYPE: DNA
<213> ORGANISM: Artificial Sequence
<220> FEATURE:
<223> OTHER INFORMATION: Primer HOXD12 forwards

<400> SEQUENCE: 43
cgcttccccc tatctcctac                                           20

```
<210> SEQ ID NO 44
<211> LENGTH: 20
<212> TYPE: DNA
<213> ORGANISM: Artificial Sequence
<220> FEATURE:
<223> OTHER INFORMATION: Primer HOXD12 reverse

<400> SEQUENCE: 44
cttcgggcgc atagaactta                                              20

<210> SEQ ID NO 45
<211> LENGTH: 20
<212> TYPE: DNA
<213> ORGANISM: Artificial Sequence
<220> FEATURE:
<223> OTHER INFORMATION: Primer HOXD13 forwards

<400> SEQUENCE: 45
ggggatgtgg ctctaaatca                                              20

<210> SEQ ID NO 46
<211> LENGTH: 20
<212> TYPE: DNA
<213> ORGANISM: Artificial Sequence
<220> FEATURE:
<223> OTHER INFORMATION: Primer HOXD13 reverse

<400> SEQUENCE: 46
aacctggacc acatcaggag                                              20
```